(12) United States Patent
Zhang et al.

(10) Patent No.: US 9,743,889 B2
(45) Date of Patent: *Aug. 29, 2017

(54) SYSTEM AND METHOD FOR DETECTING WORSENING OF HEART FAILURE BASED ON RAPID SHALLOW BREATHING INDEX

(71) Applicant: Cardiac Pacemakers, Inc., St. Paul, MN (US)

(72) Inventors: Yi Zhang, Plymouth, MN (US); Viktoria A. Averina, Roseville, MN (US); Kenneth C. Beck, Liberty, UT (US); Pramodsingh Thakur, Woodbury, MN (US); Ramesh Wariar, Blaine, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 393 days.

This patent is subject to a terminal disclaimer.

(21) Appl. No.: 14/450,728

(22) Filed: Aug. 4, 2014

(65) Prior Publication Data

US 2015/0038854 A1 Feb. 5, 2015

Related U.S. Application Data

(60) Provisional application No. 61/862,352, filed on Aug. 5, 2013.

(51) Int. Cl.
*A61B 5/00* (2006.01)
*A61B 5/0205* (2006.01)
(Continued)

(52) U.S. Cl.
CPC .......... *A61B 5/7275* (2013.01); *A61B 5/0082* (2013.01); *A61B 5/0205* (2013.01);
(Continued)

(58) Field of Classification Search
CPC ... A61B 5/7275; A61B 5/0082; A61B 5/0816; A61B 5/113; A61B 5/0205; A61B 5/091; A61B 5/0809; A61B 5/746; A61B 5/085
See application file for complete search history.

(56) References Cited

U.S. PATENT DOCUMENTS

| | | | |
|---|---|---|---|
| 4,562,841 A | 1/1986 | Brockway et al. | |
| 4,697,591 A | 10/1987 | Lekholm et al. | |

(Continued)

FOREIGN PATENT DOCUMENTS

| | | |
|---|---|---|
| CN | 105451648 A | 3/2016 |
| EP | 1151719 A2 | 11/2001 |

(Continued)

OTHER PUBLICATIONS

Dimopolou I, et al., Pattern of Breathing during Progressive Exercise in Chronic Heart Failure, IJC 81 (2001), 117-121. Abstract Only.

(Continued)

*Primary Examiner* — Peter Luong
(74) *Attorney, Agent, or Firm* — Schwegman Lundberg & Woessner, P.A.

(57) ABSTRACT

Systems and methods for detecting a worsening of patient's heart failure condition based, at least in part, on an increasing trend in a representative rapid shallow breathing index (RSBI) value over multiple days. The RSBI value may be a minimum RSBI, and more particularly may be a minimum RSBI value determined for an afternoon portion of each of the multiple days. The minimum RSBI value measured during an afternoon portion of the day may be more sensitive to changes in a patient's respiration, particularly when a patient is expected to be more active, and thus, may more readily exhibit an increasing trend when patient's heart failure is in decline.

18 Claims, 13 Drawing Sheets

(51) Int. Cl.
  *A61B 5/113* (2006.01)
  *A61B 5/08* (2006.01)
  *A61B 5/091* (2006.01)
  *A61B 5/085* (2006.01)

(52) U.S. Cl.
  CPC ............ *A61B 5/0816* (2013.01); *A61B 5/091* (2013.01); *A61B 5/113* (2013.01); *A61B 5/085* (2013.01); *A61B 5/0809* (2013.01); *A61B 5/746* (2013.01)

(56) References Cited

U.S. PATENT DOCUMENTS

| | | |
|---|---|---|
| 4,928,688 A | 5/1990 | Mower |
| 5,036,849 A | 8/1991 | Hauck et al. |
| 5,063,927 A | 11/1991 | Webb et al. |
| 5,133,353 A | 7/1992 | Hauser |
| 5,179,945 A | 1/1993 | Van Hofwegen et al. |
| 5,203,348 A | 4/1993 | Dahl et al. |
| 5,230,337 A | 7/1993 | Dahl et al. |
| 5,284,136 A | 2/1994 | Hauck et al. |
| 5,301,677 A | 4/1994 | Hsung |
| 5,313,953 A | 5/1994 | Yomtov et al. |
| 5,314,459 A | 5/1994 | Swanson et al. |
| 5,318,597 A | 6/1994 | Hauck et al. |
| 5,334,222 A | 8/1994 | Salo et al. |
| 5,360,442 A | 11/1994 | Dahl et al. |
| 5,366,496 A | 11/1994 | Dahl et al. |
| 5,372,606 A | 12/1994 | Lang et al. |
| 5,376,106 A | 12/1994 | Stahmann et al. |
| 5,388,578 A | 2/1995 | Yomtov et al. |
| 5,391,200 A | 2/1995 | KenKnight et al. |
| 5,397,342 A | 3/1995 | Heil et al. |
| 5,411,031 A | 5/1995 | Yomtov et al. |
| 5,411,525 A | 5/1995 | Swanson et al. |
| 5,468,254 A | 11/1995 | Hahn et al. |
| 5,540,727 A | 7/1996 | Tockman et al. |
| 5,545,202 A | 8/1996 | Dahl et al. |
| 5,593,431 A | 1/1997 | Sheldon |
| 5,603,732 A | 2/1997 | Dahl et al. |
| 5,620,466 A | 4/1997 | Haefner et al. |
| 5,634,938 A | 6/1997 | Swanson et al. |
| 5,662,688 A | 9/1997 | Haefner et al. |
| 5,682,898 A | 11/1997 | Aung et al. |
| 5,697,953 A | 12/1997 | Kroll et al. |
| 5,836,987 A | 11/1998 | Baumann et al. |
| 5,916,243 A | 6/1999 | Kenknight et al. |
| 5,935,081 A | 8/1999 | Kadhiresan |
| 5,957,861 A | 9/1999 | Combs et al. |
| 5,974,340 A | 10/1999 | Kadhiresan |
| 5,974,349 A | 10/1999 | Levine |
| 6,026,320 A | 2/2000 | Carlson et al. |
| 6,044,297 A | 3/2000 | Sheldon et al. |
| 6,044,298 A | 3/2000 | Salo et al. |
| 6,055,454 A | 4/2000 | Heemels |
| 6,162,183 A | 12/2000 | Hoover |
| 6,221,011 B1 | 4/2001 | Bardy |
| 6,270,457 B1 | 8/2001 | Bardy |
| 6,275,727 B1 | 8/2001 | Hopper et al. |
| 6,277,072 B1 | 8/2001 | Bardy |
| 6,280,380 B1 | 8/2001 | Bardy |
| 6,285,907 B1 | 9/2001 | Kramer et al. |
| 6,312,378 B1 | 11/2001 | Bardy |
| 6,336,903 B1 | 1/2002 | Bardy |
| 6,358,201 B1 | 3/2002 | Childre et al. |
| 6,358,203 B2 | 3/2002 | Bardy |
| 6,360,127 B1 | 3/2002 | Ding et al. |
| 6,368,284 B1 | 4/2002 | Bardy |
| 6,371,922 B1 | 4/2002 | Baumann et al. |
| 6,398,728 B1 | 6/2002 | Bardy |
| 6,409,675 B1 | 6/2002 | Turcott |
| 6,411,848 B2 | 6/2002 | Kramer et al. |
| 6,424,865 B1 | 7/2002 | Ding |
| 6,438,407 B1 | 8/2002 | Ousdigian et al. |
| 6,438,410 B2 | 8/2002 | Hsu et al. |
| 6,440,066 B1 | 8/2002 | Bardy |
| 6,449,509 B1 | 9/2002 | Park et al. |
| 6,454,719 B1 | 9/2002 | Greenhut |
| 6,459,929 B1 | 10/2002 | Hopper et al. |
| 6,480,733 B1 | 11/2002 | Turcott |
| 6,513,532 B2 | 2/2003 | Mault et al. |
| 6,527,729 B1 | 3/2003 | Turcott |
| 6,542,775 B2 | 4/2003 | Ding et al. |
| 6,564,106 B2 | 5/2003 | Guck et al. |
| 6,572,557 B2 | 6/2003 | Tchou et al. |
| 6,589,188 B1 | 7/2003 | Street et al. |
| 6,597,951 B2 | 7/2003 | Kramer et al. |
| 6,600,949 B1 | 7/2003 | Turcott |
| 6,641,542 B2 | 11/2003 | Cho et al. |
| 6,645,153 B2 | 11/2003 | Kroll et al. |
| 6,658,292 B2 | 12/2003 | Kroll et al. |
| 6,666,826 B2 | 12/2003 | Salo et al. |
| 6,705,990 B1 | 3/2004 | Gallant et al. |
| 6,708,058 B2 | 3/2004 | Kim et al. |
| 6,741,885 B1 | 5/2004 | Park et al. |
| 6,752,765 B1 | 6/2004 | Jensen et al. |
| 6,757,414 B1 | 6/2004 | Turek et al. |
| 6,773,404 B2 | 8/2004 | Poezevera et al. |
| 6,810,285 B2 | 10/2004 | Pless et al. |
| 6,830,548 B2 | 12/2004 | Bonnet et al. |
| 6,832,113 B2 | 12/2004 | Belalcazar |
| 6,856,829 B2 | 2/2005 | Ohsaki et al. |
| 6,922,587 B2 | 7/2005 | Weinberg |
| 6,961,615 B2 | 11/2005 | Kroll et al. |
| 6,993,389 B2 | 1/2006 | Ding et al. |
| 7,013,176 B2 | 3/2006 | Ding et al. |
| 7,020,521 B1 | 3/2006 | Brewer et al. |
| 7,041,061 B2 | 5/2006 | Kramer et al. |
| 7,070,568 B1 | 7/2006 | Koh |
| 7,113,823 B2 | 9/2006 | Yonce et al. |
| 7,115,096 B2 | 10/2006 | Siejko et al. |
| 7,127,290 B2 | 10/2006 | Girouard et al. |
| 7,158,830 B2 | 1/2007 | Yu et al. |
| 7,181,285 B2 | 2/2007 | Lindh et al. |
| 7,206,634 B2 | 4/2007 | Ding et al. |
| 7,228,174 B2 | 6/2007 | Burnes et al. |
| 7,260,432 B2 | 8/2007 | Kramer et al. |
| 7,306,564 B2 | 12/2007 | Nakatani et al. |
| 7,310,554 B2 | 12/2007 | Kramer et al. |
| 7,343,199 B2 | 3/2008 | Hatlestad et al. |
| 7,376,457 B2 | 5/2008 | Ross |
| 7,389,141 B2 | 6/2008 | Hall et al. |
| 7,409,244 B2 | 8/2008 | Salo et al. |
| 7,468,032 B2 | 12/2008 | Stahmann et al. |
| 7,483,743 B2 | 1/2009 | Mann et al. |
| 7,499,750 B2 | 3/2009 | Haefner et al. |
| 7,572,225 B2 | 8/2009 | Stahmann et al. |
| 7,731,663 B2 | 6/2010 | Averina et al. |
| 7,775,983 B2 | 8/2010 | Zhang et al. |
| 7,993,280 B2 | 8/2011 | Zhang et al. |
| 8,372,012 B2 | 2/2013 | Averina et al. |
| 2001/0037067 A1 | 11/2001 | Tchou et al. |
| 2001/0049470 A1 | 12/2001 | Mault et al. |
| 2002/0143264 A1 | 10/2002 | Ding et al. |
| 2003/0055461 A1 | 3/2003 | Girouard et al. |
| 2004/0116819 A1 | 6/2004 | Alt |
| 2004/0122294 A1 | 6/2004 | Hatlestad et al. |
| 2004/0127792 A1 | 7/2004 | Siejko et al. |
| 2004/0133079 A1 | 7/2004 | Mazar et al. |
| 2004/0230230 A1 | 11/2004 | Lindstrom et al. |
| 2005/0080348 A1 | 4/2005 | Stahmann et al. |
| 2005/0085734 A1 | 4/2005 | Tehrani |
| 2005/0137629 A1 | 6/2005 | Dyjach et al. |
| 2006/0020295 A1 | 1/2006 | Brockway et al. |
| 2006/0195149 A1 | 8/2006 | Hopper et al. |
| 2007/0055115 A1 | 3/2007 | Kwok et al. |
| 2007/0073168 A1* | 3/2007 | Zhang ............... A61B 5/0816 600/483 |
| 2007/0118183 A1 | 5/2007 | Gelfand et al. |
| 2007/0129643 A1* | 6/2007 | Kwok ............... A61B 5/0031 600/529 |
| 2007/0135725 A1 | 6/2007 | Hatlestad |

(56) References Cited

U.S. PATENT DOCUMENTS

| | | |
|---|---|---|
| 2007/0179389 A1 | 8/2007 | Wariar |
| 2008/0262360 A1 | 10/2008 | Dalal et al. |
| 2011/0009753 A1 | 1/2011 | Zhang et al. |

FOREIGN PATENT DOCUMENTS

| | | |
|---|---|---|
| EP | 1177764 A2 | 2/2002 |
| WO | 9833553 A1 | 8/1998 |
| WO | 0240096 A1 | 5/2002 |
| WO | 03075744 A2 | 9/2003 |
| WO | 2004062485 A2 | 7/2004 |
| WO | 2005028029 A2 | 3/2005 |
| WO | 2008085309 A1 | 7/2008 |

OTHER PUBLICATIONS

Lee et al., JAMA, 2003, 290:2581-87, Predicting Mortality Among Patients Hospitalized for Heart Failure, derivation and validation of a clinical model. Abstract Only.

Butler et al., Beta-Blocker Use and Outcomes Among Hospitalized Heart Failure Patients, Journal of the American College of Cardiology, vol. 47, No. 12, 2006, pp. 2462-2469.

Dark et al., Breathing Pattern Abnormalities and Arterial Oxygen Desaturation During Sleep in the Congestive Heart Failure Syndrome, Chest, Jun. 1987, 6:833-6. Abstract Only.

Duguet et al., Expiratory Flow Limitation as a Determinant of Orthopnea in Acute Left Heart Failure, Journal of the American College of Cardiology, vol. 35, No. 3, 2000, pp. 690-700.

Hoffman et al., Cheyne-Stokes Respiration in Patients Recovering from Acute Cardiogenic Pulmonary Edema, Chest 1990, 97:410-12. Abstract Only.

Ekman, et al., Symptoms in Patients with Heart Failure are Prognostic Predictors: Insights from COMET, J Card Fail, 11(4): 288-92, May 2005.

Silva et al., Persistent Orthopnea and the Prognosis of Patients in the Heart Failure Clinic, Congestive Heart Failure, 10(4): 177-180, 2004.

Rame et al., Outcomes after emergency department discharge with a primary diagnosis of heart failure, American Heart Journal, vol. 142(4), Oct. 2001, pp. 714-719.

Rees et al., Paroxysmal Nocturnal Dyspnoea and Periodic Respiration, The Lancet, Dec. 22-29, 1979, pp. 1315-1317. Abstract Only.

Solin et al., Effects of Cardiac Dysfunction on Non-Hypercapnic Central Sleep Apnea, Department of Respiratory Medicine, Alfred Hospital, and Department of Medicine, Monash University Medical School, Melbourne, Victoria, Australia, Apr. 10, 1997. pp. 104-110.

Tkacova et al., Left Ventricular Volume In Patients with Heart Failure and Cheyne-Strokes Respiration during Sleep, Am. Journal, Respir. Crit. Care Med., vol. 156, pp. 1549-1555, 1997.

"European Application Serial No. 14755941.3, Office Action mailed Mar. 18, 2016", 1 pg.

"European Application Serial No. 14755941.3, Response filed Sep. 29, 2016 to Communication pursuant to Rules 161(1) and 162 EPC mailed Mar. 22, 2016", 10 pgs.

"International Application Serial No. PCT/US2014/049643, International Preliminary Report on Patentability mailed Feb. 18, 2016", 6 pgs.

"International Application Serial No. PCT/US2014/049643, International Search Report mailed Oct. 27, 2014", 4 pgs.

"International Application Serial No. PCT/US2014/049643, Written Opinion mailed Oct. 27, 2014", 4 pgs.

\* cited by examiner

SYSTEM AND METHOD FOR DETECTING WORSENING OF HEART FAILURE BASED ON RAPID SHALLOW BREATHING INDEX

CROSS-REFERENCE TO RELATED APPLICATIONS

This application claims priority under 35 U.S.C. §119 to U.S. Provisional Application Ser. No. 61/862,352, filed Aug. 5, 2013, the entire disclosure of which is incorporated herein by reference.

TECHNICAL FIELD

The present disclosure generally relates to systems and methods for assessing a progression of heart failure (HF) in a heart failure patient and, more particularly detecting a worsening of patient's heart failure condition using one or more respiration related parameters.

BACKGROUND

Various disorders that affect the cardiovascular system may also impact respiration. For example, heart failure is an abnormality of cardiac function that causes cardiac output to fall below a level adequate to meet the metabolic demand of peripheral tissues. Heart failure (HF) is usually referred to as congestive heart failure due to the accompanying venous and pulmonary congestion. Heart failure may have a variety of underlying causes, including ischemic heart disease (coronary artery disease), idiopathic cardiomyopathy, hypertension (high blood pressure), and diabetes, among others.

Various types of disordered respiration are associated with HF. Respiration rate is linked to the patient's physical condition and is indicative of the patient's disease or health state. In some types of chronic diseases, changes in respiratory rate are gradual over time and may be measured over months or years. However, in heart failure decompensation, increases in respiratory rate can occur over days or weeks. Clinical data collected in the ambulatory setting has demonstrated a statistically significant difference between respiration rate distributions from healthy subjects when compared to patients.

Rapid shallow breathing (RSB) is a typical pattern associated with shortness of breath or difficult breathing (dyspnea: the subjective feeling of being out of breath) caused by heart or lung disorders, strenuous activity, high anxiety or stress. RSB is different from tachypnea (rapid breathing) and hyperpnea (deep breathing). Tachypnea and hyperpnea can occur with hyperventilation, or over breathing beyond what is required to maintain arterial blood gases within normal limits, whereas hyperpnea may be an appropriate increase in breathing such as with exercise. RSB can be associated with symptoms of shortness of breath, or dyspnea. Dyspnea derives from interactions among multiple physiological, psychological, social, and environmental factors, and may induce secondary physiological and behavioral responses. Fear or anxiety may create even more distress in dyspneic patients.

Dyspnea is among the primary factors that reduce patients' quality of life and is a primary reason why many HF patients return to the hospital following a HF decompensation episode. It is estimated that nearly one million hospital admissions for acute decompensated heart failure occur in the United States each year, which is almost double the number admitted 15 years ago. The re-hospitalization rates during the 6 months following discharge are as high at 50%. It is estimated that nearly 2% of all hospital admissions in the United States are for decompensated HF patients, and heart failure is the most frequent cause of hospitalization in patients older than 65 years. The average duration of hospitalization is about 6 days. Despite aggressive therapies, hospital admissions for HF continue to increase, reflecting the prevalence of this malady.

SUMMARY

The present disclosure generally relates to systems and methods for assessing a progression of heart failure (HF) in a patient and, more particularly detecting a worsening of patient's heart failure condition using one or more respiration related parameters.

In one example, a system for monitoring a progression of heart failure in a patient includes a sensor configured to detect respiration in a patient. The system may also include circuitry coupled to the sensor that is configured to determine a plurality of respiration rate and tidal volume measurements for each of multiple twenty-four hour periods. The system may also determine a representative RSBI value for a selected portion of each of the multiple twenty-four hour periods based, at least in part, on the corresponding plurality of respiration rate and tidal volume measurements. The system may provide an output signal indicative of a current HF status of the patient based, at least in part, on a change in the representative RSBI value over multiple twenty-four hour periods. The output signal may trigger an alert indicating that the patient is in decline.

In another illustrative embodiment, a method of determining a progression of heart failure in a patient may include: detecting respiration in a patient over multiple twenty-four hour periods using a sensor; the sensor generating signals indicative of the respiration of the patient over the multiple twenty-four hour periods; determining a plurality of respiration rate measurements and tidal volume measurements for each of the multiple twenty-four hour periods using the signals indicative of the respiration of the patient; and determining a representative RSBI value for a selected portion of each of the multiple twenty-four hour periods based, at least in part, on the corresponding plurality of respiration rate measurements and tidal volume measurements. In some instances, the method includes generating an output signal indicative of a current HF status of the patient based on a change in the representative RSBI value over multiple twenty-four hour periods. The output signal may trigger an alert indicating that the patient is in decline.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
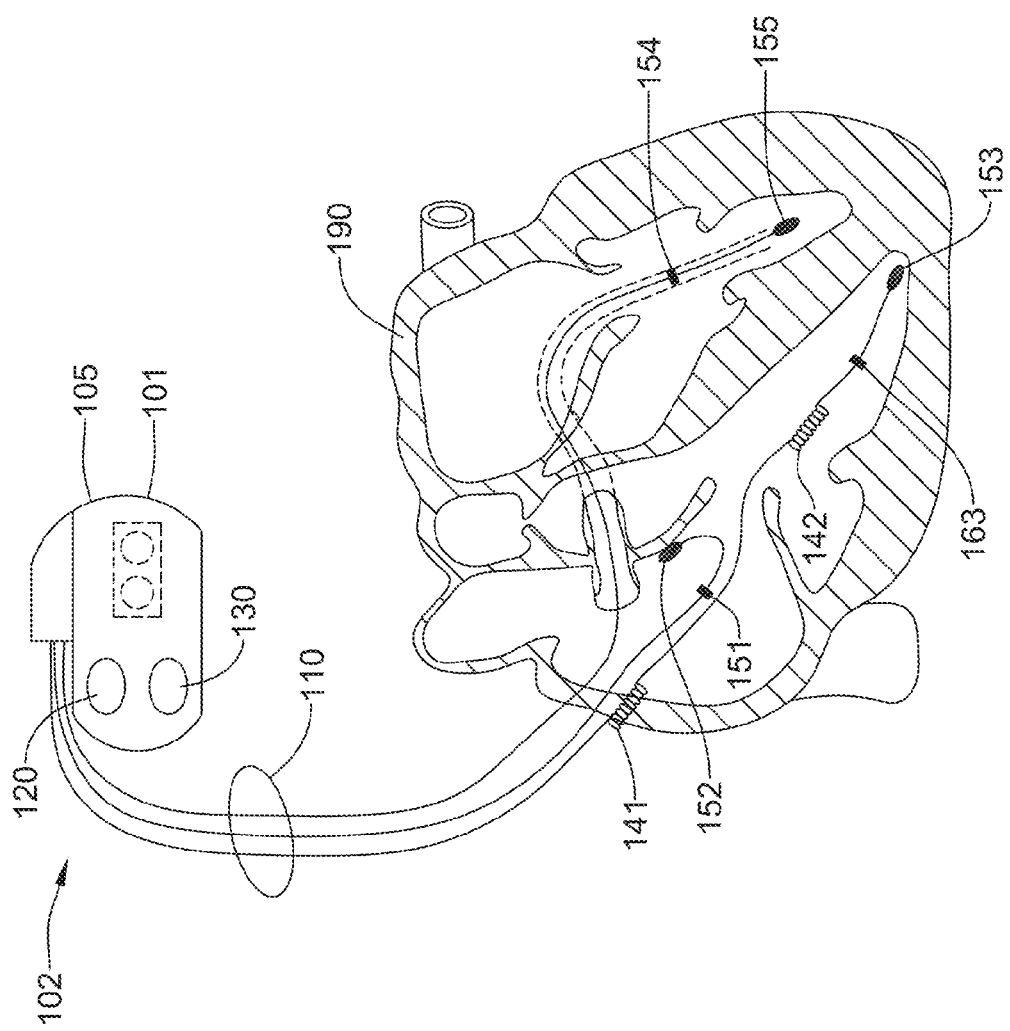
FIG. 1 is a schematic view of an implantable medical system that may be used in accordance with various embodiments described herein.

While the disclosure is amenable to various modifications and alternative forms, specifics thereof have been shown by way of example in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

Information developed from respiratory data in accordance with various embodiments provides for enhanced patient monitoring and therapy management, particularly when the status of a patient is in decline. In some cases, analysis of one or more respiration related parameters including respiration rate, respiratory interval, tidal volume, minute ventilation and/or a rapid shallow breathing index (RSBI—which may be defined as the ratio of respiration rate (RR) and relative tidal volume (TV)), may provide for detection of early onset of worsening of the patient's heart failure status. Early onset of worsening of the patient's heart failure status may be detected based, at least in part, on a trend for a respiratory related parameter including respiration rate, tidal volume, and/or a RSBI, but not limited to these. Depending upon the application, the trend may be an increasing or decreasing trend. The respiration-related data may be trended over a period of one day, one week, one month, two months, one year, etc., but not limited to these.

One day may be defined as a single twenty-four hour period. One day may also be defined as a selected portion of a single twenty-four hour period. In some cases, a twenty-four hour period may begin at midnight (i.e. 12:00 AM or 00:00 hours). In another case, a twenty-four hour period may begin at any time of the day.

Analysis of the patient's respiration and parameters related to the patient's respiration, which may be used alone or in combination with other physiological information, may trigger an alert indicating a change in the patient's status. In particular, trend analysis of one or more of the patient's respiratory related parameters such as, for example, respiration rate, respiratory interval, tidal volume, minute ventilation, and/or RSBI may trigger an alert indicating a deleterious change in the patient's heart failure status.

A wide variety of medical devices, such as cardiac sensing and/or stimulation devices or other implantable and patient-external medical devices having respiratory sensing capabilities, may be configured to monitor and/or trend one or more respiratory related parameters including respiration rate, respiratory interval, tidal volume, minute ventilation and rapid shallow breathing index. Additionally, these medical devices may be further configured to generate an output indicative of a patient's current heart failure status based, at least in part, on an analysis of a monitored trend. A non-limiting, representative list of such devices may include cardiac monitors, pulmonary monitors, pacemakers, cardioverters, defibrillators, resynchronizers, neural stimulators, and other cardiac sensing and therapy delivery devices. These devices may be configured with a variety of electrode arrangements, including surface, transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

A variety of devices other than cardiac monitoring/stimulation devices may be implemented to provide for trend parameter generation based on a patient's respiration, such as patient-external and implantable drug delivery devices equipped with a respiration sensor arrangement, for example. Such devices are referred to herein generally as a patient-implantable medical device (PIMD) for convenience. However, it may be generally understood that such a medical device and its functionality may be implemented in a patient-external device or system.

In some cases, a PIMD that may be used in accordance with the various embodiments described herein may incorporate respiration monitoring features involving dual-chamber or bi-ventricular pacing/therapy, cardiac resynchronization therapy, cardiac function optimization, and/or other HF related methodologies. For example, a PIMD may incorporate features of one or more of the following references: commonly owned U.S. Pat. Nos. 6,411,848; 6,285,907; 4,928,688; 6,459,929; 5,334,222; 6,026,320; 6,371,922; 6,597,951; 6,424,865; 6,542,775; and 7,260,432, each of which is hereby incorporated herein by reference in their entirety for all purposes. In other cases, an exemplary PIMD may be capable of implementing various functions traditionally performed by an implantable cardioverter/defibrillator (ICD), and may operate in numerous cardioversion/ defibrillation modes as are known in the art. Examples of ICD circuitry, structures and functionality, aspects of which may be incorporated into a PIMD of the present disclosure, are disclosed in commonly owned U.S. Pat. Nos. 5,133,353; 5,179,945; 5,314,459; 5,318,597; 5,620,466; and 5,662,688, each of which is hereby incorporated herein by reference in their entirety for all purposes. In still other cases, a PIMD, as described herein, may be capable of providing various pacing therapies as are known in the art, in addition to cardioversion/defibrillation therapies. Examples of pacemaker circuitry, structures and functionality, aspects of which may be incorporated in a PIMD of the present disclosure, are disclosed in commonly owned U.S. Pat. Nos. 4,562,841; 5,284,136; 5,376,106; 5,036,849; 5,540,727; 5,836,987; 6,044,298; and 6,055,454, each of which is hereby incorporated herein by reference in their entirety for all purposes. Additionally, it is generally understood that PIMD configurations may provide for non-physiologic pacing support in addition to, or to the exclusion of, bradycardia and/or anti-tachycardia pacing therapies. In still yet another example, a PIMD, as described herein, may implement diagnostic and/or monitoring functions as well as provide cardiac stimulation and/or neural stimulation therapy. Examples of cardiac monitoring circuitry, structures and functionality, aspects of which may be incorporated in a PIMD of the present disclosure, are disclosed in commonly owned U.S. Pat. Nos. 5,313,953; 5,388,578; and 5,411,031, each which are hereby incorporated herein by reference in their entirety for all purposes.

For purposes of illustration, and not of limitation, various embodiments of devices implemented in accordance with the present disclosure are described herein in the context of PIMDs that may be implanted under the skin in the chest region of a patient. A PIMD may, for example, be implanted subcutaneously such that all or selected elements of the device are positioned on the patient's front, back, side, or other body locations suitable for sensing cardiac and/or respiratory activity and/or delivering cardiac stimulation therapy. It is understood that elements of the PIMD may be located at several different body locations, such as in the chest, abdominal, or subclavian region with electrode elements respectively positioned at different regions near, around, in, or on the heart. For example, the primary housing (e.g., the active or non-active can) of the PIMD may be configured for positioning outside of the rib cage at an intercostal or subcostal location, within the abdomen, or in the upper chest region (e.g., subclavian location, such as above the third rib). In one implementation, one or more leads incorporating electrodes may be located in direct contact with the heart, great vessel or coronary vasculature, such as via one or more leads implanted by use of conventional transvenous delivery approaches. In another implementation, one or more electrodes may be located on the primary housing and/or at other locations about, but not in direct contact with the heart, great vessel or coronary vasculature. In a further implementation, for example, one or more electrode subsystems or electrode arrays may be used to sense cardiac activity and deliver cardiac stimulation energy in a PIMD configuration employing an active can or a configuration employing a non-active can. Electrodes may be situated at anterior and/or posterior locations relative to the heart. Examples of useful electrode locations and features that may be incorporated in various embodiments of the present disclosure are described in commonly owned, co-pending US Publication No. 2004/0230230 and U.S. Pat. No. 7,499,750, each of which is hereby incorporated herein by reference in their entirety for all purposes.

Additionally, in some cases, a PIMD, as described herein, may be implemented to communicate with a patient management server or network via an appropriate communications interface or an external programmer. In other cases, a PIMD, as described herein, may be used within the structure of an Advanced Patient Management (APM) system. An APM system may allow physicians to remotely and automatically monitor cardiac and respiratory functions, as well as other patient conditions. Various PIMD embodiments described herein may be used in connection with an APM system. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, each of which are hereby incorporated herein by reference in their entirety for all purposes.

Referring now to FIG. 1, an illustrative system 100 for monitoring the progression of heart failure (HF) in a patient may include a patient implantable medical device (PIMD) 102. The PIMD 102 may be configured to sense a patient's respiration and determine one or more respiratory related measurements from which a trend may be developed. Exemplary respiratory related measurements may include, but are not limited to, respiration rate, tidal volume, and a rapid shallow breath index (RSBI). A RSBI may be defined as, for example, a ratio of the respiration rate and the relative tidal volume (RR/TV). In some implementations, as shown in FIG. 1, the PIMD 102 may be a cardiac rhythm management device (CRM) including an implantable pulse generator 105 electrically and physically coupled to an intracardiac lead system 110. In another example, the lead system 110 is implanted subcutaneously.

Portions of the lead system 110 may be inserted into the patient's heart 190. In some cases, the intracardiac lead system 110 may include one or more electrodes and/or sensors configured to sense electrical cardiac activity of the heart, deliver electrical stimulation to the heart, sense the patient's transthoracic impedance, sense transthoracic total impedance, sense intracardiac impedance, sense blood (internal filling) pressure, flow, and/or temperature, sense acceleration and/or body acoustics, and/or sense other physiological parameters of interest. In addition, portions of the housing 101 of the pulse generator 105 may optionally serve as a can electrode.

Communications circuitry may be disposed within the housing 101 for facilitating communication between the pulse generator 105 and an external communication device (not shown) such as, for example, a portable or bed-side communication station, patient-carried/worn communication station (e.g., communicator), external programmer and/or Advanced Patient Management (APM) system interface. The communications circuitry may also facilitate unidirectional or bidirectional communication with one or more implanted, external, cutaneous, or subcutaneous physiologic or non-physiologic sensors, patient-input devices and/or information systems.

The pulse generator 105 may optionally incorporate a patient activity sensor 120 such as, for example, an accelerometer that may be used to sense patient activity, posture, respiration and/or cardiac related conditions. The patient activity sensor 120 may be positioned in or on the housing 101 of the pulse generator 105. In some cases, the patient activity sensor 120 may be configured to sense snoring, activity level, and/or chest wall movements associated with respiratory effort. In some cases, the patient activity sensor 120 (e.g. accelerometer) may detect respiratory, rales, coughing, cardiac (e.g. S1-S4 heart sounds, murmurs) and/or other acoustic information. A number of these physiologic variables have a systematic dependency on the phase of the respiratory cycle. For example, the pulmonic and aortic components of second heart sound (S2) systematically separate out depending upon the inspiratory/expiratory phase of the respiratory cycle. Such information may be used to develop respiration waveforms from which various respiratory parameters may be developed.

In some cases, the lead system 110 and pulse generator 105 may incorporate one or more transthoracic impedance sensors that may be used to acquire the patient's respiration waveform, or other respiration-related information. The transthoracic impedance sensor may include, for example, one or more intracardiac electrodes 141, 142, 151-155, 163 positioned in one or more chambers of the heart 190 which may be coupled to impedance drive/sense circuitry 130 positioned within the housing of the pulse generator 105. For example, in one implementation, impedance drive/sense circuitry 130 generates a current that flows through the tissue between an impedance drive electrode 151 and a can electrode on the housing 101 of the pulse generator 105. The voltage at an impedance sense electrode 152 relative to the can electrode changes as the patient's transthoracic impedance changes. The voltage signal developed between the impedance sense electrode 152 and the can electrode is detected by the impedance sense circuitry 130. Other locations and/or combinations of impedance sense and drive electrodes also may be possible.

Additionally, in some cases, the lead system 110 may include one or more cardiac pace/sense electrodes 151-155 positioned in, on, or about one or more heart chambers for sensing electrical signals from the patient's heart 190 and/or delivering pacing pulses to the heart 190. The intracardiac sense/pace electrodes 151-155, such as those illustrated in FIG. 1, may be used to sense and/or pace one or more chambers of the heart, including the left ventricle, the right ventricle, the left atrium and/or the right atrium. In some cases, the lead system 110 may include one or more defibrillation electrodes 141, 142 for delivering defibrillation/cardioversion shocks to the heart.

The pulse generator 105 may include circuitry for detecting cardiac arrhythmias and/or for controlling pacing or defibrillation therapy in the form of electrical stimulation pulses or shocks delivered to the heart through the lead system 110. The pulse generator 105 may also incorporate circuitry, structures and functionality of the implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243; 6,360,127; 6,597,951; and US Patent Publication No. 2002/0143264, each of which are hereby incorporated herein by reference in their entirety for all purposes.

Figure 2:
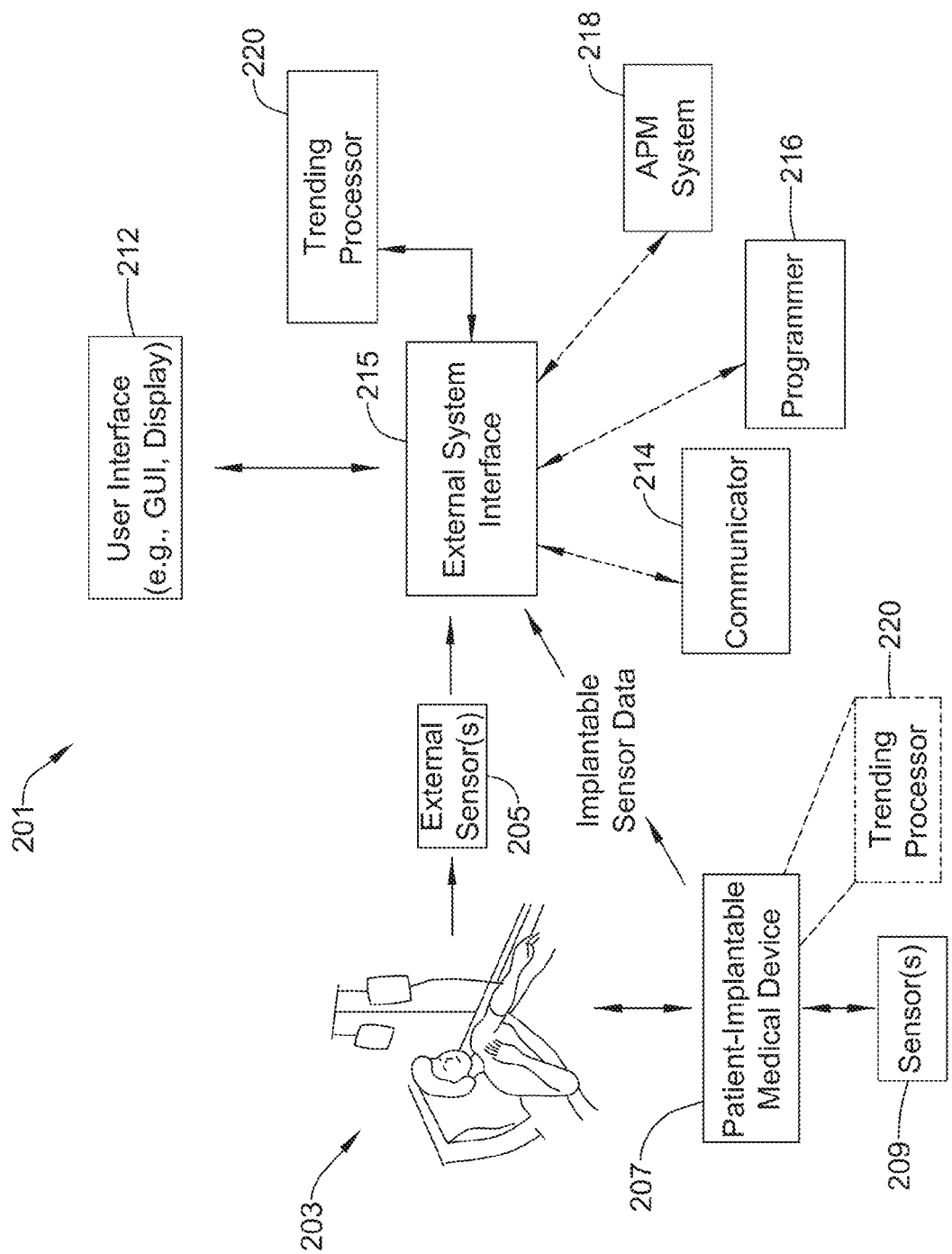
FIG. 2 is a schematic block diagram of a medical system including an implantable medical device that may be used in accordance with various embodiments described herein.

FIG. 2 is a block diagram of an illustrative system 201 for managing a patient's health based on a trend developed using respiration data in accordance with various embodiments of the disclosure as described herein. The illustrative system 201 may include a patient-implantable medical device 207 that is implanted in a patient 203. It will be generally understood that PIMD 207 may alternatively be a patient-external medical device. PIMD 207 may incorporate or, alternatively or in addition, or may be coupled to one or more implantable and/or external sensors 209. One or more of the sensors 209 may be configured to sense a respiratory parameter of the patient's breathing. Such sensors 209 may include one or more of a minute ventilation sensor, transthoracic impedance sensor, accelerometer, pressure, air flow, or other sensor capable of producing a respiratory waveform representative of the patient's breathing. A variety of external sensors 205 may also be used to sense various physiological parameters of the patient. Such external sensors 205 may include one or more of a pulse oximetry sensor, blood pressure sensor, patient temperature sensor, EKG sensor arrangement, weight scale, biomarkers, among others.

In some implementations, the system 201 may include an external system interface 215. Such an external system interface 215 may include communication circuitry configured to effect communications with PIMD 207. In some cases, external system interface 215 may be configured to effect communications with one or more external sensors 205. In some cases, the external system interface 215 may be communicatively coupled to, or integral with, one or more of a programmer 216, an advanced patient management system 218, a portable or hand-held communicator 214, or other patient-external system. The external system interface 215 may be coupled to a user interface 212, such as a graphical user interface or other interface that provides a display. User interface 212 may include a user actuatable input/output device, such as a keyboard, touch screen sensor, mouse, light pen, and the like. The user interface 212 may be used to input therapy information.

In some cases, as shown in FIG. 2, a trending processor 220 may be coupled to the external system interface 215. In other cases, the trending processor 220 may be incorporated as a component of the PIMD 207, as is shown in phantom. The trending processor 220 may perform the various trending processes described herein. In some cases, the trending processor 220 may provide one or more trend parameters developed from a plurality of respiration related measurements to the external system interface 215 for display to the physician, clinician, and/or patient via the user interface 212. These are just some examples.

Figure 3:
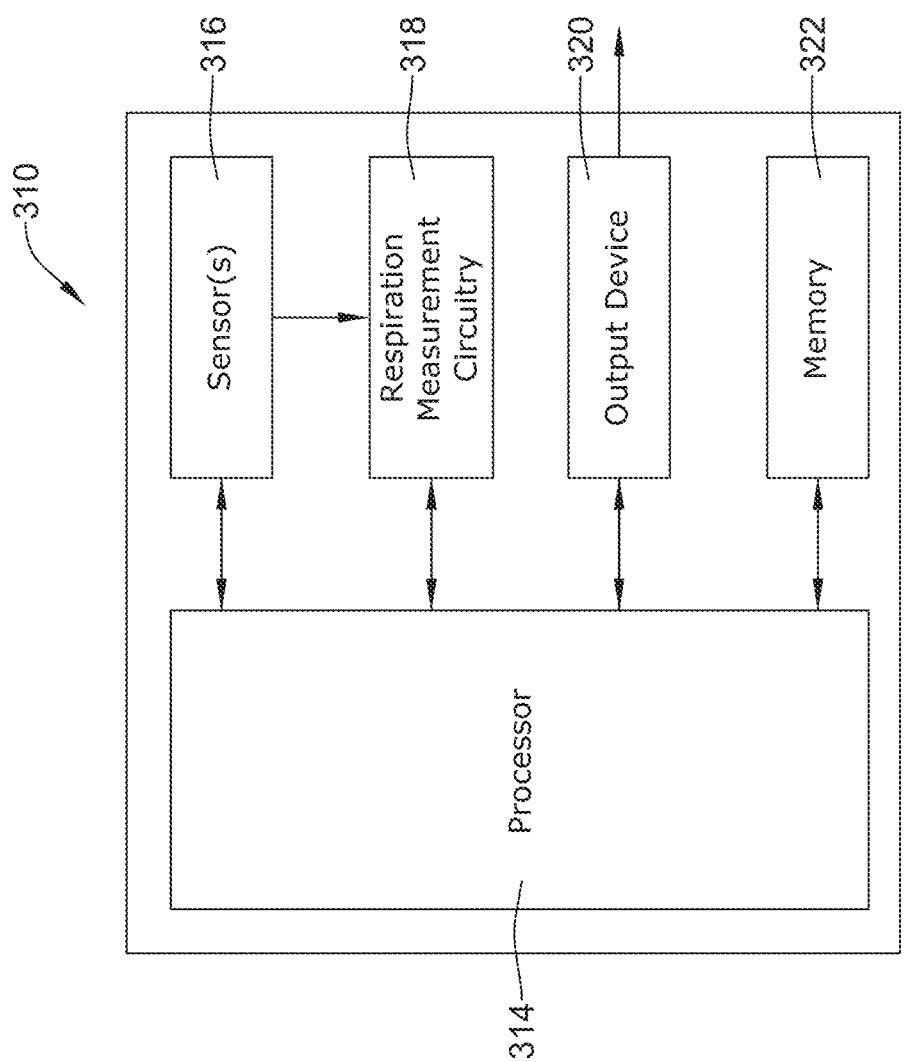
FIG. 3 is a schematic block diagram of a medical device that may be used in accordance with various embodiments described herein.

FIG. 3 is a schematic block diagram of an exemplary medical device 310 that may be used in accordance with various embodiments described herein. Medical device 310 may be an implantable medical device as described herein with reference to FIG. 1 or a patient-external medical device. In some implementations, medical device 310 may be incorporated into a medical system such as, for example, system 201 described herein with reference to FIG. 2. Medical device 310 may be configured to interface with an external advanced patient monitoring system, but this is not required.

As shown in FIG. 3, medical device 310 includes a processor 314 (e.g. microprocessor or microcontroller) coupled to one or more sensors 316, respiration measurement circuitry 318, and an output device 320. In some cases, medical device 310 may also include a local memory 322. Medical device 310 may also optionally include or be in communication with a patient activity sensor such as, for example, an accelerometer that may be used to determine a patient's activity level, and/or a posture sensor (not shown).

The one or more sensors 316 may be configured to detect a patient's respiration. In some cases, the one or more sensors 316 may be configured to detect a patient's respiration and to generate one or more signals indicative of the patient's respiration for each valid patient breath over multiple twenty-four hour periods. In some cases, the one or more sensors 316 may be configured to detect a patient's respiration and to generate one or more signals indicative of the patient's respiration for each valid patient breath over predetermined portions of multiple twenty-four hour periods. Exemplary sensors that may be incorporated into the medical device 310 may include a transthoracic impedance sensor, a minute ventilation sensor, a pressure sensor, an accelerometer, a flow sensor, and/or any other suitable sensor or sensor combination, as desired.

The respiration circuitry 318 may be configured to receive the signals generated by the one or more respiration sensors 316, and to determine respiration related measurements using the signals indicative of patient respiration for each of the multiple twenty-four hour periods. In some case, the respiration circuitry 318 may be configured to determine a plurality of respiration related measurements for each of the multiple twenty-four hour periods including respiration rate measurements, tidal volume measurements, and/or rapid shallow breathing index (RSBI) values, but these are just some examples. In some cases, the RSBI may be defined as a ratio between the respiration rate and the relative tidal volume (e.g. RR/TV) over a corresponding time period or over one or more breaths. In some cases, the respiration circuitry 318 may include signal conditioning circuitry which may include a filter, a signal amplifier, and/or an analog to digital converter.

The processor 314, which is shown coupled to the one or more sensors 316 and the respiration measurement circuitry 318, may be configured to execute one or more software applications stored in the memory 322 for monitoring and/or trending one or more respiration related parameters based, at least in part, on the patient's respiration detected by the one or more sensors 316. More particularly, in some cases, the processor 314 may be configured to determine a representative respiration rate value, a representative tidal volume value, and/or a representative RSBI index value based, at least in part, on the plurality of respiration related measurements determined by the respiration circuitry 318. The representative respiration rate value may include one or more of a minimum respiration rate, an average respiration rate, a median respiration rate, a maximum respiration rate, a standard deviation of respiration rate, and an inter-quartile range of respiration rate. In some cases, the representative respiration rate value represents a minimum respiration rate (RRmin) or a lower percentile of respiratory rate. Similarly, the representative tidal volume value may be include one or more of a minimum tidal volume value, an average tidal volume value, a median tidal volume value, a maximum tidal volume value, a standard deviation of tidal volume value, and an inter-quartile range of tidal volume value. In some cases, the representative tidal volume value represents a maximum tidal volume value (TVmax) or a higher percentile of tidal volume, and more particularly, a maximum of averaged tidal volume values (max avg TV) over a predetermined period of time. A representative RSBI value may be calculated using any combination of a minimum respiration rate, median respiration rate, average respiration rate, certain percentiles of respiration rate or a maximum respiration rate and a minimum tidal volume value, an average tidal volume value, a median tidal volume value, certain percentile of tidal volume, a maximum tidal volume value, and/or any other suitable value as desired. In some implementations, a representative RSBI value may be determined using a minimum respiration rate and a maximum tidal volume (RRmin/TVmax). In another implementation, a representative RSBI value may be determined by taking an average of the RSBI index (e.g., RR/TV avg) over a predetermined period of time. Additionally, it has been found that a minimum or a lower percentile of RSBI value over a particular time period may be more sensitive to changes, particularly a change (e.g. declining) in heart failure status.

In some instances, the processor 314 may be configured to generate a distribution of the multiple respiration rate measurements and/or tidal volume measurements determined by the respiration measurement circuitry 318. From the distribution, the processor 314 may determine a representative respiration rate value and/or tidal volume value. For example, in one implementation, a representative tidal volume value may be determined based on a distribution of the plurality of tidal volume measurements. The representative tidal volume value may be determined based on an upper percentile of the plurality of tidal volume measurements. Similarly, a representative respiration rate value may be determined based on an upper percentile of the plurality of respiration rate measurements.

An upper percentile for the measurement distribution may be defined as any percentile ranging from a fifty-first percentile to a one hundred percentile. More particularly, an upper percentile may be defined as any percentile ranging from: a sixtieth percentile to a one hundred percentile; a seventieth percentile to a one hundred percentile; an eightieth percentile to a one hundred percentile; an eighty-fifth percentile to a one hundred percentile; and a ninetieth percentile to a one hundred percentile. In some cases, the upper percentile for either the representative respiration rate value or representative tidal volume value may range from the ninetieth percentile to a one hundred percentile.

A lower percentile for the measurement distribution may be defined as any percentile ranging from a zero percentile to a fiftieth percentile. More particularly, a lower percentile may be defined as any percentile ranging from: a zero percentile to a forty-fifth percentile; a zero percentile to a fortieth percentile; a zero percentile to thirtieth percentile; a zero percentile to twentieth percentile; and a zero percentile to a fifteenth percentile. In some cases, a lower percentile may be defined as any percentile below about a twenty-fifth percentile of the measurement distribution.

In some instances, a representative RSBI value may be calculated using any combination of an upper or lower percentile of the plurality of the respiration rate measurements and an upper or lower percentile of the plurality of the tidal volume measurements, or an upper or lower percentile of the plurality of ratios, RR/TV determined by the respiration measurement circuitry. In one example, a representative RSBI value may include a lower percentile of a plurality of respiration rate measurements and an upper percentile of a plurality of tidal volume measurements. In another example, a representative RSBI value may include both an upper percentile of a plurality of respiration rate measurements and an upper percentile of a plurality of tidal volume measurements. In another example, RSBI may be an upper or lower percentile of the plurality of individual RR/TV values.

In some instances, that one-to-one pairing of tidal volume measurements and respiration measurements (pairs of nearly simultaneously measured TV/RR measurements) may be preserved in deriving the representative RSBI measurement. The representative RSBI value could be determined using some upper percentile of a plurality of tidal volume measurements and the set of respiration rate values that correspond to the TV samples that satisfy the chosen upper percentile. In another instance a statistic on the respiration rate could be used to sub-select paired samples of TV and RR to derive the representative RSBI value.

In some instances, that one-to-one pairing of tidal volume measurements and respiration measurements (pairs of nearly simultaneously measured TV/RR measurements) may be used to generate instantaneous RSBI measurements for the corresponding periods of TV and RR measurements. The representative RSBI value could be determined using a lower percentile or a minimum of the plurality of RSBI measurements of a predetermined period of time.

The processor 314 may be configured to determine a representative respiration rate value, a tidal volume value, and/or an RSBI value, as discussed herein, for each twenty-four hour period of a plurality of twenty-four hour periods. The multiple twenty-four hour periods may be successive twenty-four hour periods, and may, in some cases, precede a current day or a heart failure event, but this is not required. In some instances, a predetermined portion of the twenty-four hour periods may be used. Additionally, the processor 314 may be configured to trend the representative respiration rate value, tidal volume value, and/or RSBI value over multiple twenty-four hour periods (e.g. over multiple days). In some cases, the processor 314 may be configured to determine a representative respiration rate value, a tidal volume value and/or a RSBI value for a selected portion (e.g. afternoon) of a twenty-four hour period, and to trend the representative respiration value, tidal volume value and/or RSBI value determined for the selected portion of a twenty-four hour period over multiple twenty-four hour periods.

In some implementations, a twenty-four period may include a morning portion, an afternoon portion, an evening portion, and a night portion. In some cases, the morning portion may range from about 06:00 to about 12:00 hours or another other periods within this range or a period after the patient wakes up; the afternoon portion may range from about 12:00 hours to about 18:00 hours or another periods within this range; the evening portion may range from about 18:00 hours to about 00:00 hours or any other periods within this range; and the night portion may range from about 00:00 hours to about 06:00 hours or any other periods within this range or a period when the patient is asleep. In some cases the time window for the different portions might be specified by a user. In some cases, the selected portion of each twenty-four hour period may correspond to an afternoon portion.

In some cases, the selected portion of each twenty-four hour period may correspond to a morning portion. In other cases, the selected portion of each twenty-four hour period may correspond to a morning portion and an afternoon portion. In still other instances, the selected portion of each twenty-four hour period may include a morning portion, an afternoon portion, and an evening portion. In many cases, the selected portion of each twenty-four hour period may exclude the night portion of each twenty-four hour period, but this is not required. In some cases, the selected portion may start from the time point that the patient wakes up in the morning. This wake-time may either be user input via a programming device or automatically determined using device based sensors.

In some cases, the selected portion may end at the time point that the patient goes to sleep in the evening. This sleep-time may either be user input via a programming device or automatically determined using device based sensors. The wake-time and sleep-time may also vary from one 24-hour period to another 24-hour period.

The exclusion of the night portion from a monitored twenty-four hour period may be counterintuitive to what one of skill in the art may expect to be a preferred portion of the day to monitor trends in tidal volume and/or an RSBI index. For example, one of skill in the art may expect the preferred portion of the day to be the night portion, when the patient is at rest, is less active and has less postural variation (i.e. asleep) thus, the signal is cleaner. Moreover, orthopnea (short of breath when lying down), a cardinal sign of heart failure occurs when the patient is in a supine position. It is more likely to be observed during night when the patient is sleeping. In addition, it has been observed that at least some signs or symptoms of heart failure such as, for example, apnea and paroxysmal nocturnal dyspnea, among others, may occur in the evening portion. However, data collected through clinical study indicates that portions of the day, excluding the evening and/or night portion, may be better for evaluating tidal volume and RSBI for the purposes of determining a declining status of a patient. In particular, the collected data indicates that an afternoon portion of a twenty-four hour period may be the optimal portion of the day for evaluating tidal volume and RSBI for determining a declining status of a patient. This may be due to a combination of the patient's physiology and the patient's activity levels. Typically, a patient is most active during an afternoon portion of the day. As such, the greatest tidal volumes may be experienced by the patient during that portion of the day. As a patient is in decline, the patient may become less active over time, including during the afternoon portion of the day when the patient is typically expected to be most active, and the patient's tidal volumes during that portion of the day may begin to decline faster during this period from their historical baseline. Since tidal volume and RSBI are related, an increasing trend may also be more readily observed in a patient's RSBI values during the portions of the day excluding the night portion, and in some cases, during an afternoon portion of the day.

In some implementations, a representative respiration rate value, representative tidal volume value, and/or a representative RSBI value may be a value determined by the processor 314 based, at least in part, on a plurality of respiration related measurements collected over multiple twenty-four hour periods. In particular, the value determined by the processor 314 may be based, at least in part, on a plurality of respiration related measurements for a selected portion of each twenty-four hour period of which the measurement data are collected, as discussed herein. In some cases, the plurality of tidal volume measurements may be collected over an afternoon portion of a twenty-four hour period. The plurality of tidal volume values determined over each of the multiple twenty-four hour periods may be used to determine a long term aggregate for a tidal volume over the multiple twenty-four hour periods and a short term aggregate tidal volume that may then be compared to the long term aggregate. In some cases, the long term and short term tidal volume aggregates may be any statistical measure of data such as, for example, a median, a mean, a minimum, a maximum, an upper percentile, a lower percentile tidal volume value, and/or any other suitable aggregate that may be determined from a plurality of representative tidal volume values collected over different time windows having different durations. This may be useful where, for example, there is a large volume of respiration related parameter data collected for the individual patient over several months. In some cases, the tidal volume aggregate may be based on a maximum tidal volume value or an averaged tidal volume value.

In some implementations, a plurality of tidal volume measurements may be used to determine a long term aggregate tidal volume over a first time window having a first duration, and a short term aggregate tidal volume over a second time window having a second duration. In many cases, the first time window may be a historical time window that precedes the second time window, and may span a period of time ranging from at least five days up to about six months or more. This is just one example. It will generally be understood that a variety of respiration related parameter data may be collected for longer periods of time as necessary or desired or as the data storage capabilities of the medical device (e.g. medical device 310) permit. With the expanding use of cloud storage technology, the amount of data that may be collected and stored may be essentially unlimited.

In one example, a long term aggregate may be determined from a plurality of tidal volume values collected over a period of time of at least five days and up to about six months, and a short term aggregate may be determined over a period of time of less than about two weeks, and perhaps a period of time of less than about one week. Additionally, the short term aggregate may be determined over a period of time that directly precedes the current day, and as such may be considered a near term window. Additionally, the first time window over which a long term aggregate is determined may precede the second time window over which a short term aggregate is determined by at least one day. More particularly, the first time window may precede the second time window by a period of time of about one month. In one instance, the first time window may be separated from and precede the second time window by a time period of at least two weeks (i.e. 14 days). In another instance, the first and the second time window may overlap.

Similarly, in some implementations, the representative RSBI value determined by the processor 314 may be an RSBI value based on a plurality of respiration rate measurements and tidal volume measurements collected for each of multiple twenty-four hour periods. In some cases, the plurality of respiration rate and tidal volume measurements may be collected for a selected portion of each of the multiple twenty-four hour periods, such as for example, an afternoon portion as discussed herein. The plurality of respiration rate and tidal volume measurements may be used to determine the representative RSBI value for a selected portion of each of the multiple twenty-four hour periods. The representative RSBI value for the selected portion of each of the multiple twenty-four hour periods may be used to determine a long term aggregate for the RSBI over multiple twenty-four hour periods, and a short term aggregate for the RSBI. The short term aggregate of the RSBI may be compared to the long term aggregate. The long term and short term RSBI aggregate may be any statistical measure of data such as, for example, a median, a mean, a minimum, a maximum, an upper percentile, a lower percentile, and/or another other aggregate of the RSBI that may be determined from a plurality of representative RSBI values collected over different time windows having different durations. This may be useful where, for example, there is a large volume of respiration related parameter data collected for the individual patient over several months. In some cases, the RSBI aggregate may be based on a minimum of a plurality of ratios of averaged respiration rate and maximum tidal volume. In some cases, the aggregate RSBI value may be based on an average minimum respiration rate and maximum tidal volume, but this is just one example. In some cases, the RSBI aggregate may be based on the average of a plurality of representative RSBI values.

In some implementations, a plurality of representative RSBI values may be used to determine a long term RSBI aggregate over a first time window having a first duration, and a short term RSBI aggregate over a second time window having a second duration. In many cases, the first time window is a historical time window that precedes the second time window, and may span a period of time ranging from at least five days up to about six months. This is just one example. It will generally be understood that a variety of respiration related parameter data may be collected for longer periods of time as necessary or desired or as the data storage capabilities of the medical device (e.g. medical device 310) permit. With the expanding use of cloud storage technology, the amount of data that may be collected and stored may be essentially unlimited.

In one RSBI example, a long term RSBI aggregate may be determined from a plurality of RSBI values collected over a period of time of at least five days and up to about six months, and a short term aggregate may be determined over a period of time of less than about two weeks, and perhaps a period of time of less than about one week. Additionally, the short term aggregate may be determined over a period of time that directly precedes the current day, and as such may be considered a near term window. Additionally, the first time window over which a long term aggregate is determined may precede the second time window over which a short term aggregate is determined by at least one day. More particularly, the first time window may precede the second time window by a period of time of about one month (ranging from two weeks to two months). For example, in one instance, the first time window may be separated from and precede the second time window by a time period of at least three weeks.

Figure 4:
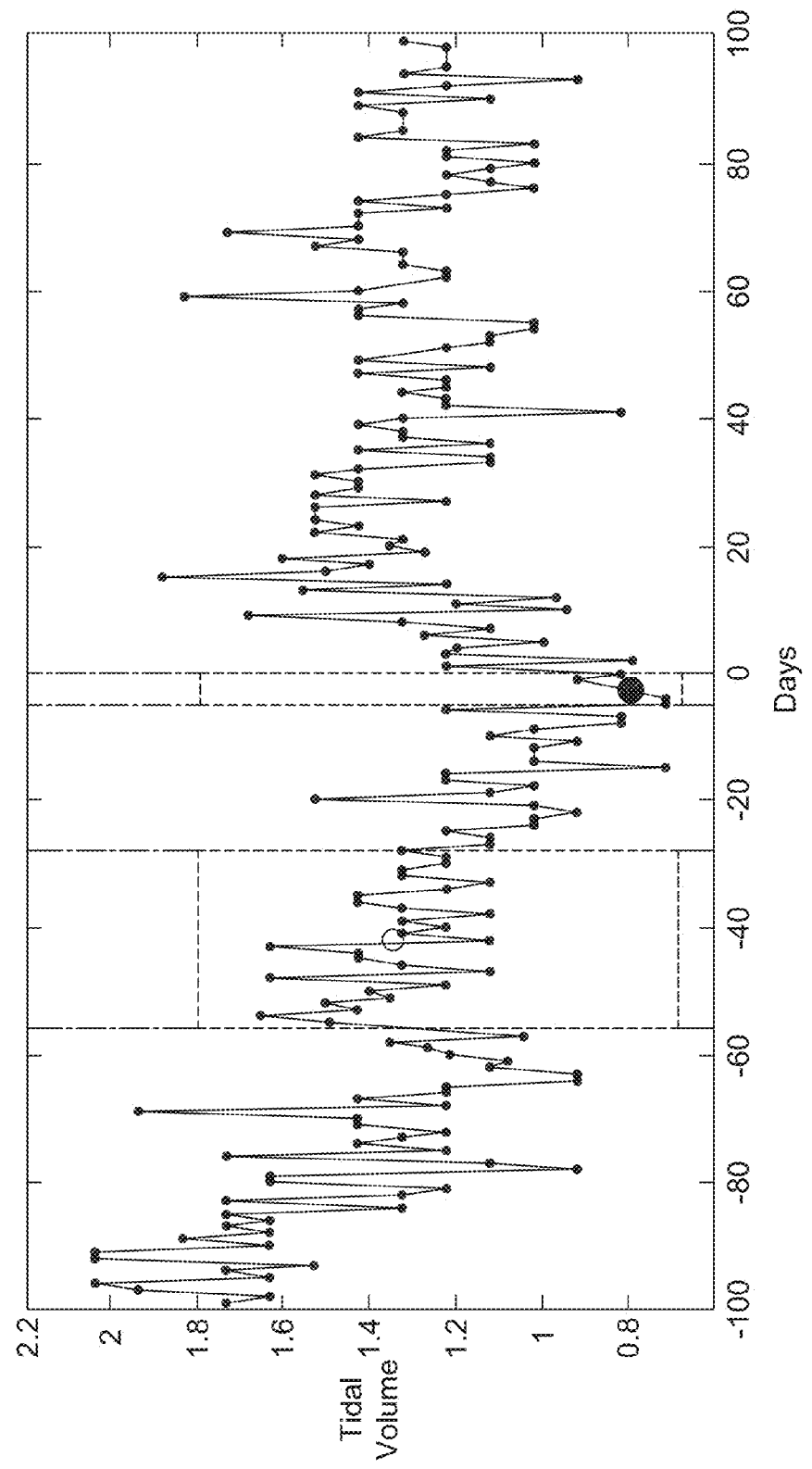
FIG. 4 shows a graphical representation of a representative tidal volume value trended over multiple days preceding a current day.

FIG. 4 shows a graphical representation of a tidal volume value trended over multiple twenty-four hour periods preceding a current day. The tidal volume value that is plotted for each day may be, for example, any one of a maximum tidal volume value detected for that day, an average tidal volume value for that day, a tidal volume value representing an upper percentile of the plurality of tidal volume measurements or a lower percentile of the plurality of tidal volume measurements for the day, or any other tidal volume value for that day. As shown in FIG. 4, there is a decreasing trend in the tidal volume value. A declining trend in tidal volume may indicate a shallower breathing pattern, thus the patient's current heart failure status may be in decline or worsening.

Figure 5:
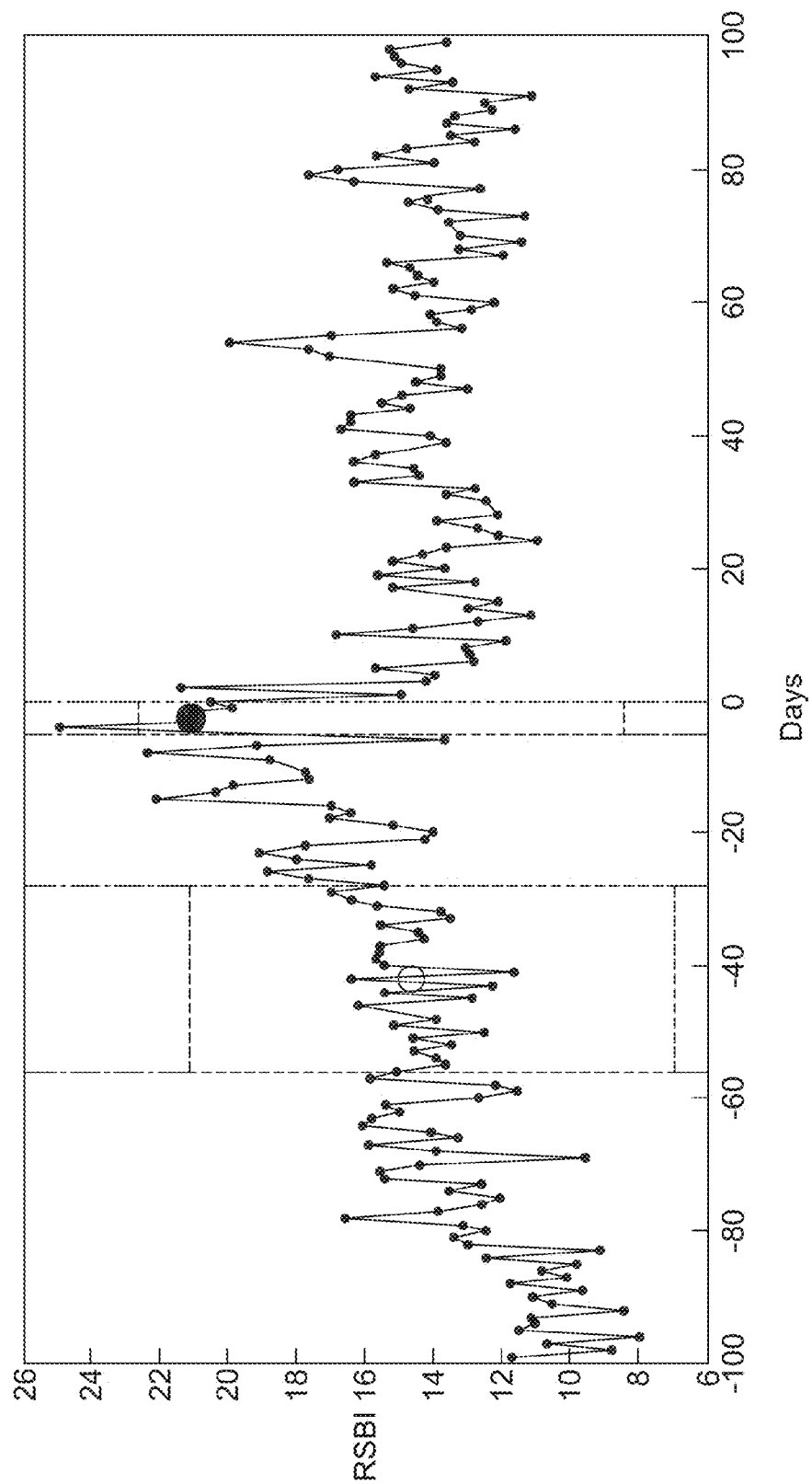
FIG. 5 is a graphical representation of a representative rapid shallow breathing index (RSBI) value trended over multiple days preceding a current day.

Similarly, FIG. 5 shows a graphical representation of an RSBI value trended over multiple twenty-four hour periods preceding a current day. The RSBI value may be an RSBI value of a plurality of RSBI measurements for a given day, an RSBI measurement representing an upper percentile of a plurality of RSBI measurements or a lower percentile of a plurality of RSBI values for a given day, or an aggregate RSBI value for a given day. These are just some examples. Like the representative tidal volume value, a representative RSBI value may be trended for a selected portion of each multiple twenty-four hour periods such as, for example, an afternoon portion, as discussed herein. FIG. 5 shows an increasing trend in the representative RSBI value. As stated herein, an increasing trend in RSBI may indicate a worsening of the rapid shallow breathing pattern, thus the patient's current heart failure status may be in decline or worsening.

In some cases, the processor 314 may be configured to perform a trend analysis on the data, such as the data presented in the graphs shown in FIGS. 4 and 5. For example, referring to the data shown in FIG. 4, the processor 314 may be configured to determine a first tidal volume aggregate over a first time window having a first duration and a second tidal volume aggregate over a second time window having a second duration, and to determine a relationship between the first tidal volume aggregate and the second tidal volume aggregate. The tidal volume aggregate determined for each of the first and second time windows may be an aggregate tidal volume value as discussed herein. In some cases, the first time window may be a historical time window having a duration of at least five days and up to about six months and, in some instances, may be considered a long term window. The second time window may have a duration of less than about two weeks and more particularly a period of time of less than about one week. Additionally, the second window may correspond to a period of time that directly precedes the current day and/or includes the current day, and as such may be considered a near term window. Typically, the first and second time windows do not overlap, but this is not required. For example, the first time window may precede the second time window by at least one day. More particularly, the first time window may precede the second time window by a period of time of about one month. For example, in one instance, the first time window may be separated from and precede the second time window by a time period of at least two weeks (i.e. 14 days). However, these are just some examples.

In some implementations, the processor 314 may be configured to determine the relationship between the first tidal volume aggregate determined for the first time window and the second tidal volume aggregate determined for the second time window, and based at least in part on the determined relationship, identify a current trend in a patient's heart failure status. For example, the processor 314 may be programmed to determine a relationship between the first tidal volume aggregate and the second tidal volume aggregate by subtracting the first tidal volume aggregate from the second tidal volume aggregate. In another example, the processor 314 may be programmed to characterize the relationship between the first tidal volume aggregate and the second tidal volume aggregate by determining a fractional difference between the first tidal volume aggregate and the second tidal volume aggregate. In yet another example, the processor 314 may be configured to characterize the relationship between the first tidal volume aggregate and the second tidal volume aggregate by determining a slope of a line on a graph extending from the first tidal volume aggregate to the second tidal volume aggregate, with the x-axis corresponding to time. With respect to FIG. 5, it will be generally understood that the processor 314 may be programmed to perform similar trend analyses of a plurality of RSBI values determined for a patient over a period of time, and to use one or more trend analyses to identify the patient's current heart failure status.

In some implementations, the processor 314 may be configured to generate an output signal via the output device 320 indicative of the patient's current HF status based on an analysis of the trend. For example, the processor 314 may be configured to trigger an alert based on an increasing trend in the representative respiratory rate value, a decreasing trend in the representative tidal volume value, and/or an increasing trend in the representative RSBI value determined over multiple twenty-four hour periods. For example, an alert may be triggered when changes in the representative tidal volume value and/or representative RSBI value exceed a pre-determined threshold value. In some cases, the processor 314 may be configured to trigger an alert based on a determined relationship between a first respiration related parameter aggregate determined over a first time window and a second respiration related aggregate determined over a second time window, as discussed herein with reference to FIG. 4. The pre-determined threshold value may be determined based, at least in part, on respiration related parameter data collected for the individual patient, and may be unique to each individual patient. In some cases, the alert may provide an indication to the patient and/or clinician of an impending heart failure event enabling the patient and/or clinician to seek treatment possibly preventing or lessening the severity of a more serious heart failure decompensation event. The alert may be displayed to the patient or clinician via a user interface of an external patient monitoring device and/or may be transmitted by the output device 320 using a telemetry link or other wireless communication link to another device utilized by the patient clinician. In some implementations, the alert may include a message that may be displayed visually to the patient or clinician via a user interface of an external patient monitoring system or other device. In other cases, the alert may be a visual alert such as, for example, a flashing or blinking light, symbol or message. In still other cases, the alert may be an audible alert such as, for example, an audible announcement, warning bell or alarm, or audible beeps. It will be generally understood that the alert may be a combination of any of the alerts as discussed herein.

Figure 6:
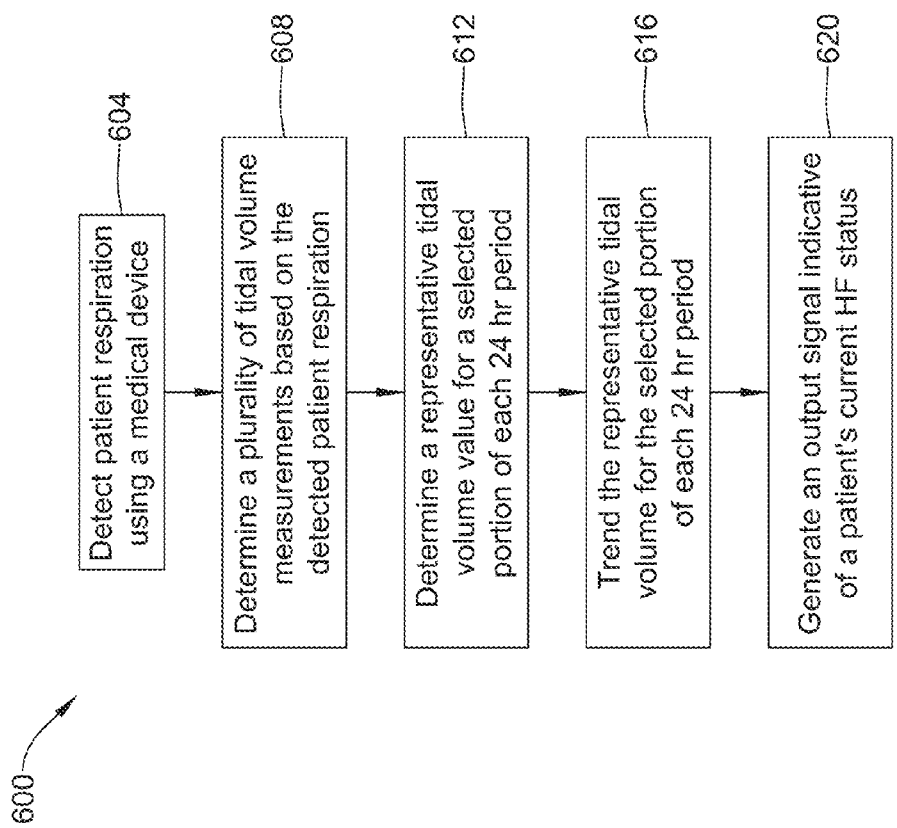
FIG. 6 is a flow diagram of a method that may be implemented by a medical device such as shown in FIG. 3.

FIG. 6 is a flow chart of an illustrative method 600 for monitoring a progression of heart failure (HF) in a patient using a tidal volume parameter. According to the method 600, patient respiration may be monitored and detected using a medical device (Block 604), such as an implantable or patient-external medical device 310 described herein. The medical device 310 may include a sensor configured to detect the patient's respiration and to generate a signal indicative of the patient's respiration. Exemplary sensors may include a transthoracic impedance sensor, a minute ventilation sensor, a pressure sensor, an accelerometer, a flow sensor, and/or any other suitable sensor or sensor combination, as desired. In some cases, patient respiration may be monitored and detected over multiple days. One day may be defined as a single twenty-four hour period. One day may be defined as a selected portion of a single twenty-four hour period. In many cases, patient respiration may be monitored and detected over multiple, successive twenty-four hour periods, but this is not required.

Respiration circuitry may be used to determine a plurality of tidal volume measurements for each twenty-four hour period using the signals indicative of patient respiration (Block 608). The tidal volume measurements may be determined for each valid patient breath. A representative tidal volume value may be determined based, at least in part, on the plurality of tidal volume measurements for each twenty-four hour period. In some cases, the representative tidal volume value can be any one of a minimum tidal volume value (TVmin), a median tidal volume value (TVmed), an average tidal volume value, or a maximum tidal volume value (TVmax), an upper percentile or a lower percentile tidal volume value, for each twenty-four hour period. A processor coupled to the sensor and the respiration measurement circuitry may determine a representative tidal volume value for a selected portion each twenty-four hour period based, at least in part, on the plurality of tidal volume measurements (Block 612). In some cases, a twenty-four period may include a morning portion, an afternoon portion, an evening portion, and a night portion. The morning portion may range from about 06:00 to about 12:00 hours, or any time period within that window, or a period after the patient wakes up; the afternoon portion may range from about 12:00 hours to about 18:00 hours or any time period within that window; the evening portion may range from about 18:00 hours to about 00:00 hours or any time period within that window; and the night portion may range from about 00:00 hours to about 06:00 hours or any time period within that window or a period when the patient is asleep. In some cases, the selected portion of each twenty-four hour period may correspond to an afternoon portion. In some cases, the selected portion of each twenty-four hour period may correspond to a morning portion. In other cases, the selected portion of each twenty-four hour period may correspond to a morning portion and an afternoon portion. In still other cases, the selected portion of each twenty-four hour period may include a morning portion, an afternoon portion, and an evening portion. In many cases, the selected portion of each twenty-four hour period for which a representative tidal volume value such as, for example, TVmax, is determined excludes the night portion of a twenty-four hour period.

The processor may trend the representative tidal volume values over multiple twenty-four hour periods and, in some cases, may determine a patient's heart failure status based on the trend (Block 616). In some cases, the processor may generate an output signal indicative of a patient's current heart failure signal based on a change (e.g. decrease) in the representative tidal volume value over multiple twenty-four hour periods (Block 620). In some cases, the output signal may trigger an alert, which may indicate that the patient's heart failure status is in decline.

Figure 7:
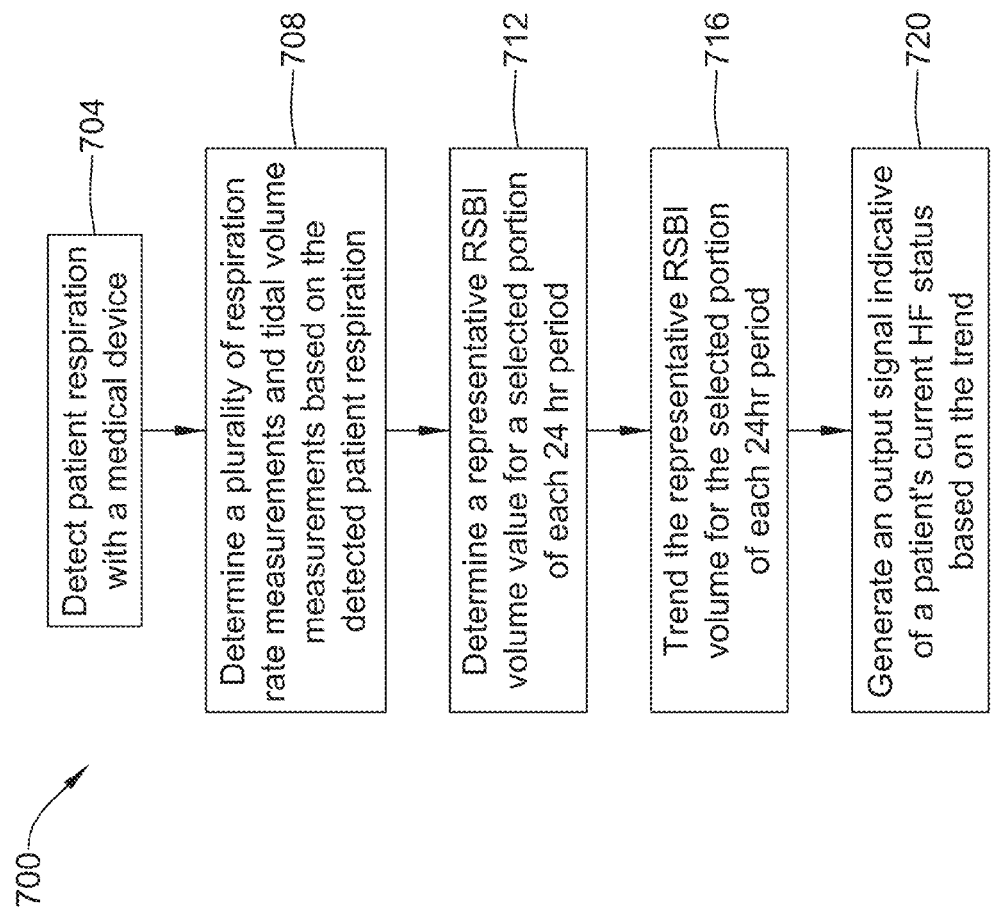
FIG. 7 is a flow diagram of another method that may be implemented by a medical device such as shown in FIG. 3.

FIG. 7 is a flow chart of a method 700 of monitoring a progression of heart failure (HF) in a patient based, at least in part, on a rapid shallow breathing index (RSBI) parameter. According to the method 700, patient respiration may be monitored and detected using a medical device (Block 704), such as an implantable or patient-external medical device 310 described herein. The medical device 310 may include a sensor configured to detect the patient's respiration and to generate a signal indicative of the patient's respiration. Exemplary sensors may include a transthoracic impedance sensor, a minute ventilation sensor, a pressure sensor, an accelerometer, a flow sensor, and/or any other suitable sensor or sensor combination, as desired. In some cases, patient respiration may be monitored and detected over multiple days. One day may be defined as a single twenty-four hour period. In many cases, patient respiration may be monitored and detected over multiple, successive twenty-four hour periods, but this is not required.

Respiration circuitry may be used to determine a plurality of respiration rate measurements and tidal volume measurements for a selected portion of each twenty-four hour period based using the signals indicative of patient respiration (Block 708). These measurements may be used to determine RSBI values for each valid patient breath. A representative RSBI value may be determined based, at least in part, on the plurality of respiration rate measurements and tidal volume measurements for each twenty-four hour period. The representative RSBI value may be calculated using any combination of a minimum respiration rate, median respiration rate, average respiration rate, or a maximum respiration rate and a minimum tidal volume value, an average tidal volume value, a median tidal volume value, a maximum tidal volume value, and/or any other suitable respiration parameter. In some implementations, the representative RSBI value may be determined using a minimum respiration rate and a maximum tidal volume (RRmin/TVmax). In some implementations, the representative RSBI value for a twenty-four hour period may be determined by taking a minimum or a lower percentile of a plurality of ratios of RR and TV over a pre-determined portion of the twenty-four hour period.

In some implementations, a representative RSBI value may be determined for a selected portion each twenty-four hour period based, at least in part, on the plurality of respiration rate measurements and tidal volume measurements (Block 712). In some cases, a twenty-four period may include a morning portion, an afternoon portion, an evening portion, and a night portion. The morning portion may range from about 06:00 to about 12:00 hours or any time period within that window or a period after the patient wakes up; the afternoon portion may range from about 12:00 hours to about 18:00 hours or any time period within that window; the evening portion may range from about 18:00 hours to about 00:00 hours or any time period within that window; and the night portion may range from about 00:00 hours to about 06:00 hours or any time period within that window or a period when the patient is asleep. In some cases, the selected portion of each twenty-four hour period may correspond to an afternoon portion. In some cases, the selected portion of each twenty-four hour period may correspond to a morning portion. In other cases, the selected portion of each twenty-four hour period may correspond to a morning portion and an afternoon portion. In still other cases, the selected portion of each twenty-four hour period may include a morning portion, an afternoon portion, and an evening portion. In many cases, the selected portion of each twenty-four hour period for which a representative RSBI value is determined excludes a night portion of a twenty-four hour period.

The processor may trend the representative RSBI values over multiple twenty-four hour periods and, in some cases, may determine a patient's heart failure status based on the trend (Block 716). In some cases, the processor may generate an output signal indicative of a patient's current heart failure signal based on a change (e.g. increase) in the representative RSBI over multiple twenty-four hour periods (Block 720). The output signal may trigger an alert, which may indicate that the patient's heart failure status is in decline.

EXAMPLES

Example 1

In a study, 160 heart failure patients were followed for 333±78 days. During the course of the study, a trend of 20-minute averages of tidal volume (TV) values was collected for each patient. Out of that trend a total of 144 composites were generated by choosing a window within a 24-hour period and a statistic (minimum, mean, or maximum) to apply to that window. Windows were chosen of four different durations: 6, 12, 18, and 24 hours. The start of each window was selected to range from 12 am to 10 pm, with a 2-hour increment. The total number of daily composite trends derived is: 3×4×12=144.

Figure 8:
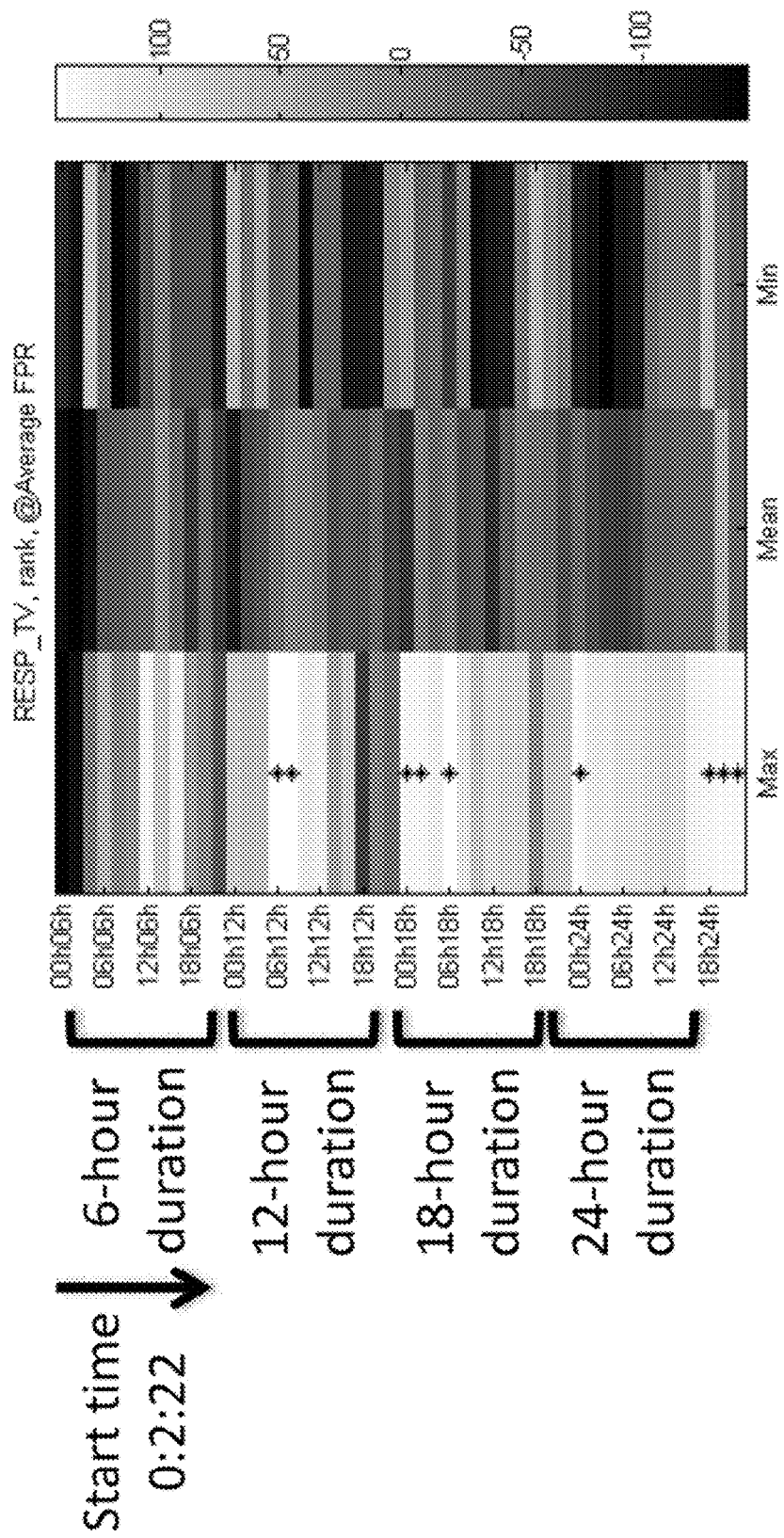
FIG. 8 is a plot that charts the maximum, mean, and minimum tidal volumes at an average false positive rate of 1.5 false positives per patient year and a sensitivity ranging from 0 to 0.5.

All 144 trends were ranked based on their relative performance to each other. The ranking was determined as detailed below. For each daily composite trend a predictor trend was calculated: on each day a fractional difference between an average of the long-term window (baseline) and short-term window (last 5 days) was calculated: (LTA−STA)/LTA, where LTA is a long-term aggregate, STA is a short-term aggregate. A range of long-term windows was used to generate several predictor trends. The start of the long-term windows varied from 15 to 65 days prior (at 5-day increments) and the end of the window varied from 5 to 30 days prior (at 5-day increments). For each predictor trend (entire set of long-term windows), two sensitivities were calculated at 1 and 1.5 false positive rate. A smaller set of 9 long-term windows with the greatest overall sensitivity values was selected for each trend (one set per FPR). Next, sets for each pair of daily composite trends were compared using a t-test. If the test was significant, one trend was considered to outperform the other. Otherwise, they were considered to be equivalent. The rank of each daily composite trend is equal to the number of the other trends it has outperformed. The higher the ranking, the better the trend. An average rank between two FPR values was then determined. FIG. 8 shows the average ranks across all 144 trends. The labels on the y-axis of the figure MMhNNh indicate the selected window, where MM is the start of the window and NN is the duration of the window, in hours. The labels on the x-axis of the figure indicate the statistics used for the window. As shown in FIG. 8, the maximum tidal volume during the afternoon portion of the twenty-four hour period provides the maximum sensitivity.

Figure 9:
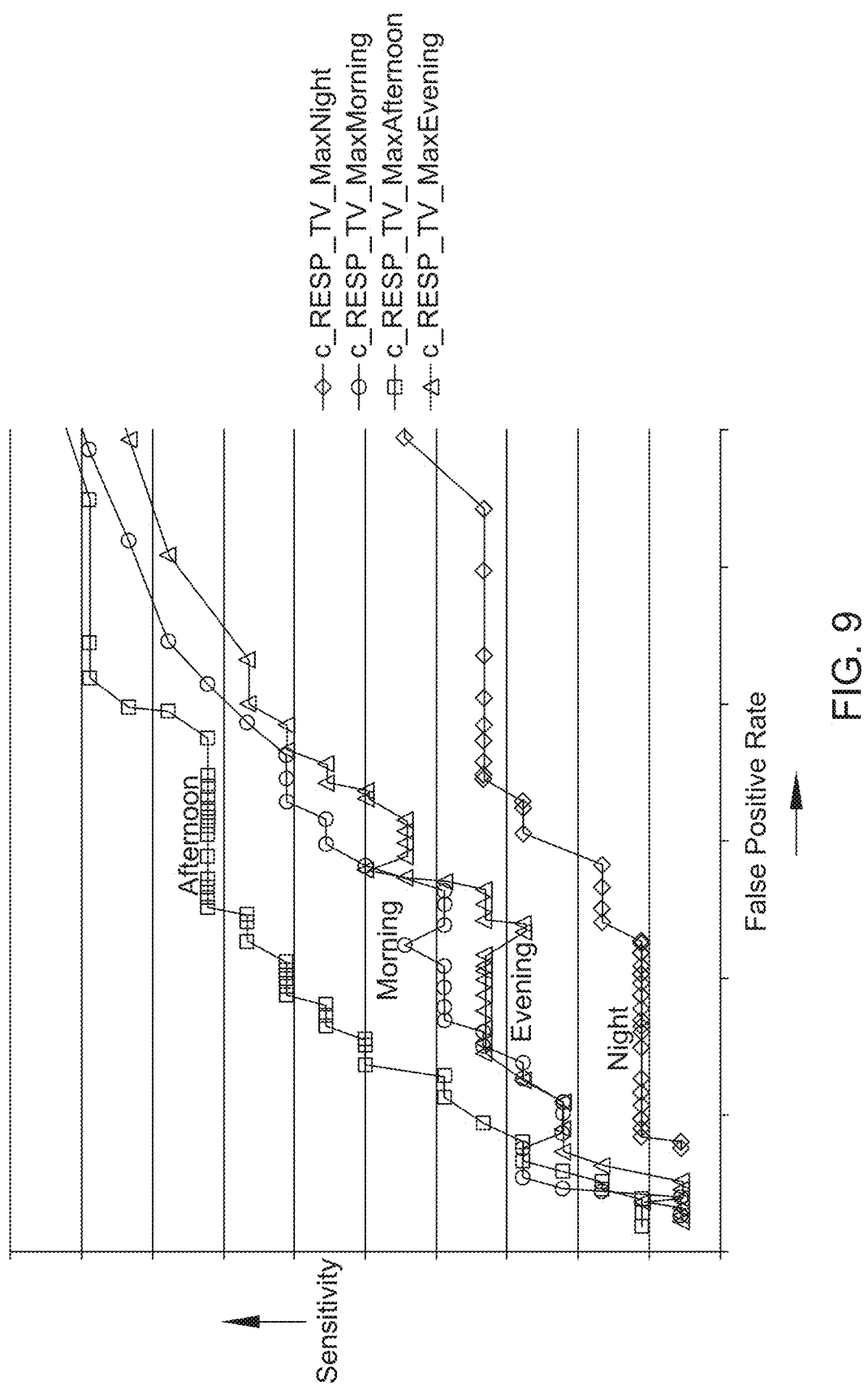
FIG. 9 is shows a relative operating characteristic (ROC) curve showing the relationship between maximum tidal volume and different portions of the day.

FIG. 9 shows a receiver operating characteristic (ROC) curve using the data from the study. The ROC curve was generated for the maximum tidal volumes at an increasing false positive rate (x axis) and an increasing sensitivity ranging (y axis) for each different portion of the day (e.g. afternoon, morning, evening, and night). As can be seen, a maximum tidal volume in the afternoon portion of the day provides the best performance.

Figure 10:
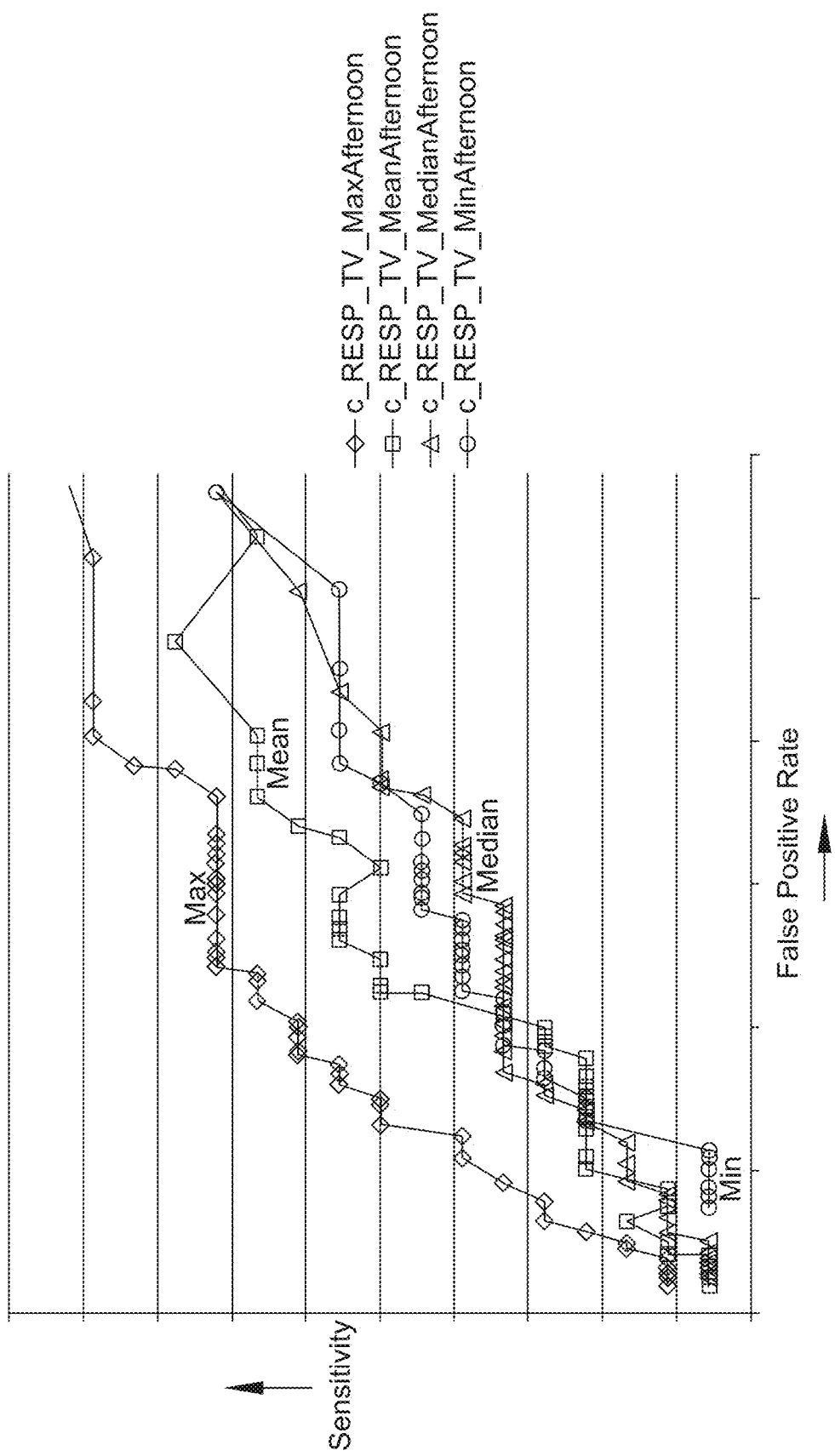
FIG. 10 is a relative operating characteristic (ROC) curve showing the relationship between different portions of the day and maximum tidal volume, minimum tidal volume, mean tidal volume, and minimum tidal volume.

Another ROC curve, as shown in FIG. 10, was generated to evaluate the maximum tidal volumes, minimum tidal volumes, mean tidal volume values and median tidal volume values recorded for an afternoon portion of the day at an increasing false positive rate (x axis) and an increasing sensitivity (y axis). The ROC curve shown in FIG. 10 confirms that a maximum tidal volume may exhibit a greater sensitivity for the same false positive rate to changes in a patient's heart failure status during an afternoon portion of the day than the mean, median or minimum tidal volume values.

Example 2

In the same study, trends in RSBI values were evaluated for each of the 160 heart failure patients. In the study, RSBI was defined as the ratio between a respiration rate and a tidal volume. During the study, trends of 20-minute averages of tidal volume (TV) and respiratory rate (RR) values were collected for each patient. RSBI trend was generated by taking the ratio of RRs and TVs. Out of that trend a total of 144 composites were generated by choosing a window within a 24-hour period and a statistic (minimum, mean, or maximum) to apply to that window. Windows were chosen of four different durations: 6, 12, 18, and 24 hours. The start of each window was selected to range from 12 am to 10 pm, with a 2-hour increment. The total number of daily composite trends derived is: 3×4×12=144.

Figure 11:
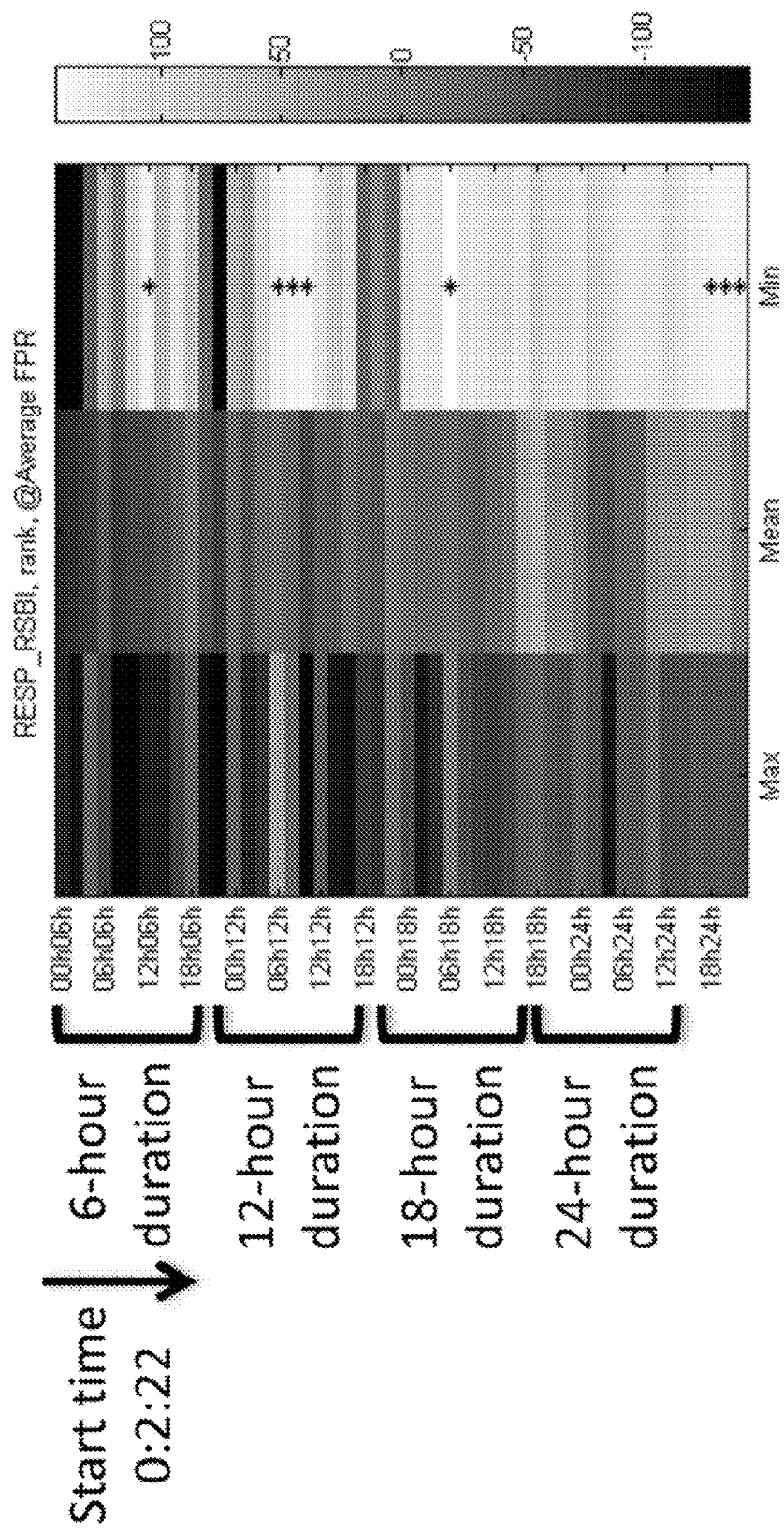
FIG. 11 is a color plot showing maximum, mean, and minimum rapid shallow breathing index values at an average false positive rate of 1.5 false positives per patient year and a sensitivity ranging from 0 to 0.5.

All 144 trends were ranked based on their relative performance to each other. The ranking was determined as detailed below. For each daily composite trend a predictor trend was calculated: on each day a fractional difference between an average of the long-term window (baseline) and short-term window (last 5 days) was calculated: (LTA−STA)/LTA, where LTA is a long-term aggregate, STA is a short-term aggregate. A range of long-term windows was used to generate several predictor trends. The start of the long-term windows varied from 15 to 65 days prior (at 5-day increments) and the end of the window varied from 5 to 30 days prior (at 5-day increments). For each predictor trend (entire set of long-term windows), two sensitivities were calculated at 1 and 1.5 false positive rate. A smaller set of 9 long-term windows with the greatest overall sensitivity values was selected for each trend (one set per FPR). Next, sets for each pair of daily composite trends were compared using a t-test. If the test was significant, one trend was considered to outperform the other. Otherwise, they were considered to be equivalent. The rank of each daily composite trend is equal to the number of the other trends it has outperformed. The higher the ranking, the better the trend. An average rank between two FPR values was then determined. FIG. 11 shows the average ranks across all 144 trends. The labels on the y-axis of the figure MMhNNh indicate the selected window, where MM is the start of the window and NN is the duration of the window, in hours. The labels on the x-axis of the figure indicate the statistics used for the window. From the plot, the minimum RSBI shows a better sensitivity to changes in a patient's heart failure status during the afternoon portion of the twenty-four hour period.

Figure 12:
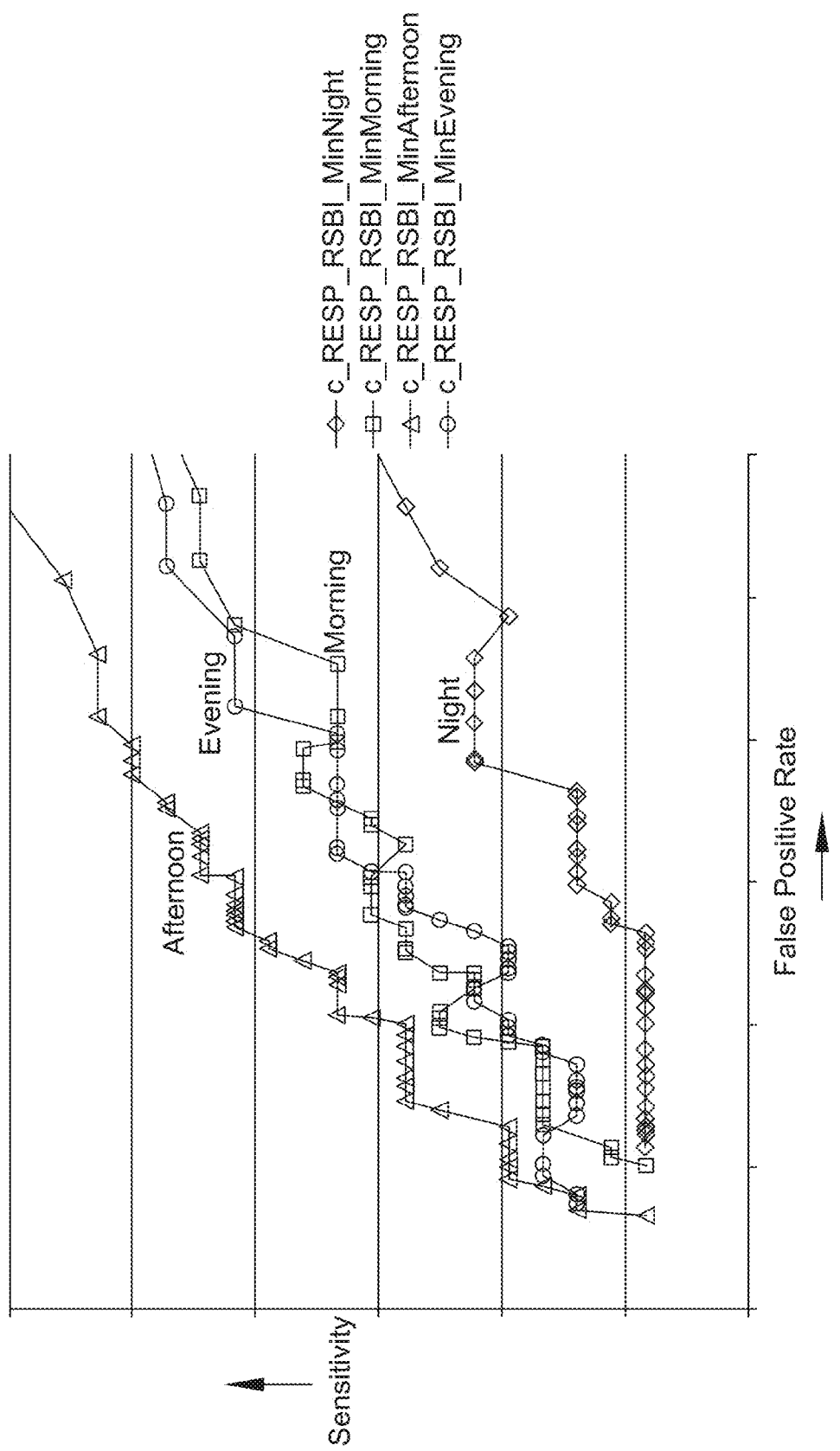
FIG. 12 is a relative operating characteristic (ROC) curve showing the relationship between minimum RSBI values and different portions of the day.

Turning now to FIG. 12, which shows a receiver operating characteristic (ROC) curve, which was generated for the minimum RSBI at an increasing false positive rate (x-axis) and an increasing sensitivity (y axis) for each different period of the day (e.g. afternoon, morning, evening, and night). As can be seen from the ROC curve in FIG. 12, a minimum RSBI in the afternoon portion of the day may be the most sensitive to changes in a patient's heart failure status at the same false positive rate.

Figure 13:
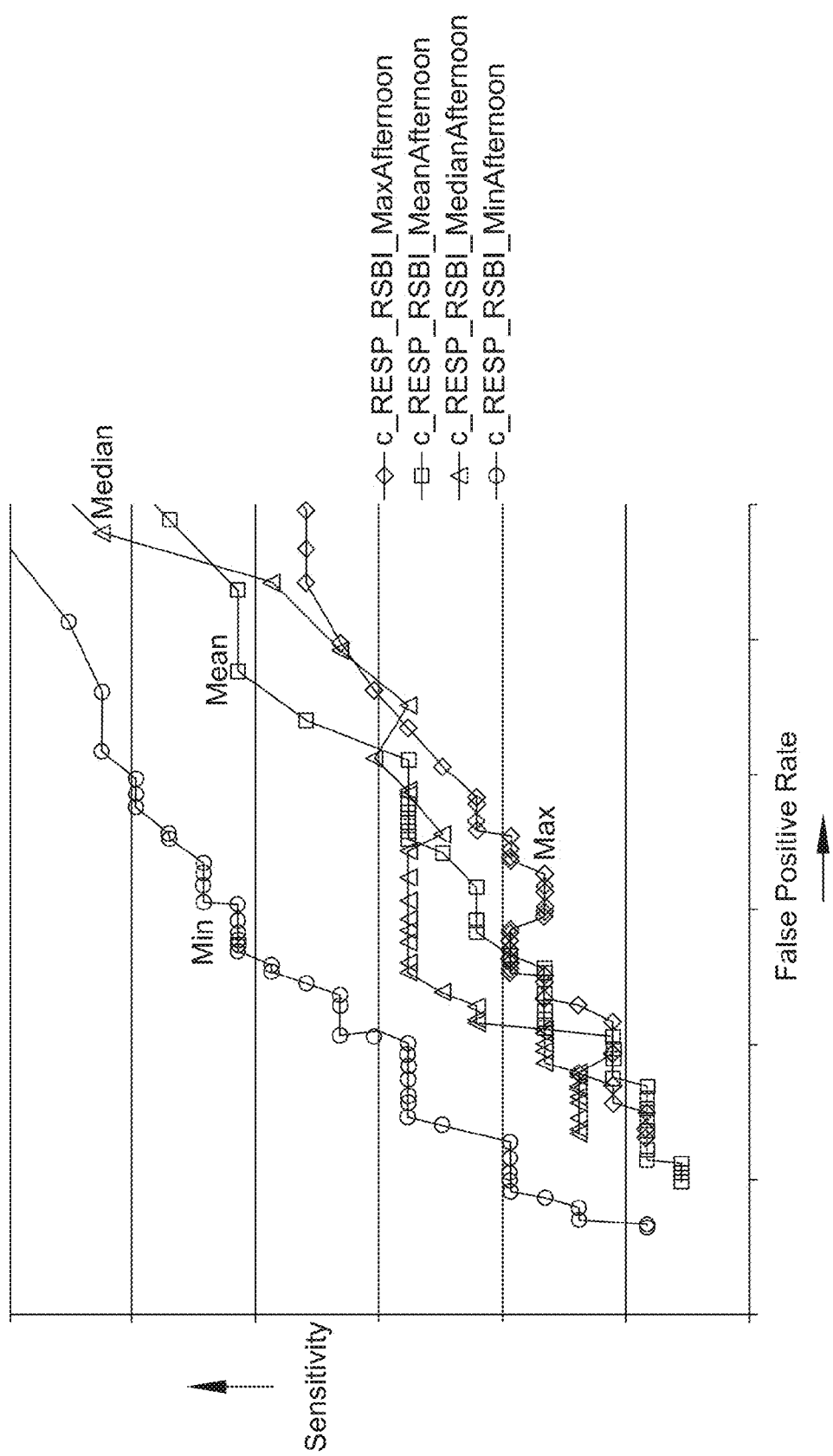
FIG. 13 is a relative operating characteristic (ROC) curve showing the relationship between different portions of the day and a maximum RSBI, a minimum RSBI, a mean RSBI, and a minimum RSBI.

Another ROC curve, as shown in FIG. 13, was generated to evaluate the maximum RSBI, minimum RSBI, mean RSBI and median RSBI recorded for an afternoon portion of the day at an increasing false positive rate (x axis) and an increasing sensitivity (y axis). The ROC curve shown in FIG. 13 confirms that a minimum RSBI may exhibit a greater sensitivity to changes in a patient's heart failure status at the same false positive rate during an afternoon portion of the day than the mean, median or maximum RSBI.

Those skilled in the art will recognize that the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A system for monitoring a progression of heart failure in a patient, the system comprising:
 a sensor configured to provide one or more signals indicative of respiration of a patient;
 circuitry coupled to the sensor, the circuitry configured to:
  determine a plurality of respiration rate and tidal volume measurements during each of a plurality of twenty-four hour periods using the one or more signals indicative of the respiration of the patient;
  determine a rapid shallow breathing index (RSBI) value for a selected portion of each of a plurality of the twenty-four hour periods based, at least in part, on one or more of the corresponding plurality of the respiration rate and tidal volume measurements;
  determine a first RSBI aggregate based, at least in part, on the RSBI values that fall within a first time window having a first duration;
  determine a second RSBI aggregate based, at least in part, on the RSBI values that fall within a second time window having a second duration, wherein the first duration is different than the second duration;
  determine a relationship between the first RSBI aggregate determined for the first time window and the second RSBI aggregate determined for the second time window; and an output coupled to the circuitry for providing an output signal indicative of an HF status of the patient based, at least in part, on the determined relationship between the first RSBI aggregate determined for the first time window and the second RSBI aggregate determined for the second time window, wherein the RSBI aggregates for the selected portion of each of the plurality of twenty-four hour period are determined, in part, by a ratio between the corresponding plurality of respiration rate and tidal volume measurements, and wherein the RSRI aggregates for the selected portion of each of the plurality of twenty-four hour period are defined by a minimum or a lower percentile of the plurality of the ratios between the corresponding plurality of respiration rate measurements and the corresponding plurality of tidal volume measurements.

2. The system according to claim 1, wherein the sensor comprises at least one of an impedance sensor, a capacitance sensor, an accelerometer, a displacement sensor, an optical sensor and a pressure sensor.

3. The system according to claim 1, wherein the relationship between the first RSBI aggregate determined for the first time window and the second RSBI aggregate determined for the second time window is determined by subtracting the first RSBI aggregate determined for the first time window from the second RSBI aggregate determined for the second time window.

4. The system according to claim 1, wherein the relationship between the first RSBI aggregate determined for the first time window and the second RSBI aggregate determined for the second time window is characterized by determining a fractional difference between the first RSBI aggregate determined for the first time window and the second RSBI aggregate determined for the second time window.

5. The system according to claim 1, wherein the first duration and second duration are measured in a number of twenty-four hour periods.

6. The system according to claim 1, wherein the first time window and the second time window do not overlap.

7. The system according to claim 1, wherein the selected portion of each of the twenty-four hour periods corresponds to an afternoon portion, a morning portion, or an evening portion.

8. The system according to claim 1, wherein the selected portion of each of the twenty-four hour periods corresponds to a morning portion and an afternoon portion.

9. The system according to claim 1, wherein the selected portion of each of the twenty-four hour periods excludes a period when the patient is asleep.

10. The system according to claim 1, wherein the first and second RSBI aggregates are defined by a ratio between a minimum respiration rate and a maximum tidal volume.

11. The system according to claim 1, wherein the RSBI aggregates for the selected portion of each of the plurality of twenty-four hour period are defined by a ratio between a lower value of the corresponding plurality of respiration rate measurements and an upper value of the corresponding plurality of tidal volume measurements.

12. A system for monitoring a progression of heart failure in a patient, the system comprising:
a sensor configured to detect respiration in a patient and configured to generate signals indicative of the patient's respiration over multiple twenty-four hour periods,
circuitry coupled to the sensor, the circuitry configured to:
determine a plurality of respiration rate and tidal volume measurements for each of multiple twenty-four hour periods using the signals indicative of the respiration of the patient;
determine a representative RSBI value for a selected portion of each of the multiple twenty-four hour periods based, at least in part, on the corresponding plurality of respiration rate and tidal volume measurements;
determine a first RSBI aggregate based, at least in part, on the RSBI values that fall within a first time window having a first duration;
determine a second RSBI aggregate based, at least in part, on the RSBI values that fall within a second time window having a second duration, wherein the first duration is different than the second duration;
determine a relationship between the first RSBI aggregate determined for the first time window and the second RSBI aggregate determined for the second time window; and
an output coupled to the circuitry for providing an output signal indicative of a current heart failure status of the patient based on a change in the representative RSBI value over multiple twenty-four hour periods,
wherein the RSBI aggregates for the selected portion of each of the plurality of twenty-four hour period are determined, in part, by a ratio between the corresponding plurality of respiration rate and tidal volume measurements, and wherein the RSBI aggregates for the selected portion of each of the plurality of twenty-four hour period are defined by a minimum or a lower percentile of the plurality of the ratios between the corresponding plurality of respiration rate measurements and the corresponding plurality of tidal volume measurements.

13. The system according to claim 12, wherein the circuitry is configured to determine a representative RSBI value based on a lower value of the plurality of respiration rate measurements and an upper value of plurality of tidal volume measurements for the selected portion of each of the multiple twenty-four hour periods.

14. The system according to claim 12, wherein the circuitry is configured to determine a representative RSBI value based on a lower value of a plurality of the ratios between the corresponding plurality of respiration rate measurements and the corresponding plurality of tidal volume measurements for the selected portion of each of the multiple twenty-four hour periods.

15. The system according to claim 12, wherein the change in the representative RSBI value is determined based on a difference between a long term aggregate of the representative RSBI value and a short term aggregate of the representative RSBI value.

16. The system according to claim 12, wherein the selected portion corresponds to at least one of a morning portion, an afternoon portion and an evening portion of each of the multiple twenty-four hour periods.

17. A method of determining a progression of heart failure in a patient, the method comprising:
detecting respiration in a patient over multiple twenty-four hour periods using a sensor;
the sensor generating signals indicative of the respiration of the patient over the multiple twenty-four hour periods;
determining a plurality of respiration rate measurements and tidal volume measurements for each of the multiple twenty-four hour periods using the signals indicative of the respiration of the patient;

determining a representative RSBI value for a selected portion of each of the multiple twenty-four hour periods based, at least in part, on the corresponding plurality of respiration rate measurements and tidal volume measurements;

determining a first RSBI aggregate based, at least in part, on the RSBI values that fall within a first time window having a first duration;

determining a second RSBI aggregate based, at least in part, on the RSBI values that fall within a second time window having a second duration, wherein the first duration is different than the second duration;

determining a relationship between the first RSBI aggregate determined for the first time window and the second RSBI aggregate determined for the second time window; and generating an output signal indicative of a current heart failure status of the patient based on a change in the representative RSBI value over multiple twenty-four hour periods, wherein the RSBI aggregates for the selected portion of each of the plurality of twenty-four hour period are determined, in part, by a ratio between the corresponding plurality of respiration rate and tidal volume measurements, and wherein the RSBI aggregates for the selected portion of each of the plurality of twenty-four hour period are defined by a minimum or a lower percentile of the plurality of the ratios between the corresponding plurality of respiration rate measurements and the corresponding plurality of tidal volume measurements.

18. The method according to claim 17, wherein the selected portion of each of the multiple twenty-four hour periods excludes a period when the patient is asleep.

* * * * *